US011118085B2

(12) United States Patent
Nose et al.

(10) Patent No.: US 11,118,085 B2
(45) Date of Patent: Sep. 14, 2021

(54) WATER-REPELLENT SUBSTRATE

(71) Applicant: DAIKIN INDUSTRIES, LTD., Osaka (JP)

(72) Inventors: Masatoshi Nose, Osaka (JP); Tsuneo Yamashita, Osaka (JP); Kaori Ozawa, Osaka (JP); Hisashi Mitsuhashi, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 131 days.

(21) Appl. No.: 16/335,726

(22) PCT Filed: Sep. 22, 2017

(86) PCT No.: PCT/JP2017/034366
§ 371 (c)(1),
(2) Date: Mar. 22, 2019

(87) PCT Pub. No.: WO2018/056410
PCT Pub. Date: Mar. 29, 2018

(65) Prior Publication Data
US 2019/0322893 A1 Oct. 24, 2019

(30) Foreign Application Priority Data

| Sep. 23, 2016 | (JP) | JP2016-185759 |
| Apr. 20, 2017 | (JP) | JP2017-083841 |
| Jun. 14, 2017 | (JP) | JP2017-116961 |
| Aug. 1, 2017 | (JP) | JP2017-149207 |

(51) Int. Cl.
| C09D 171/02 | (2006.01) |
| C03C 17/32 | (2006.01) |
| C09D 5/00 | (2006.01) |
| C23C 14/12 | (2006.01) |
| C07D 251/10 | (2006.01) |
| C07D 251/34 | (2006.01) |
| C07D 405/14 | (2006.01) |
| C07F 7/18 | (2006.01) |

(52) U.S. Cl.
CPC ............ *C09D 171/02* (2013.01); *C03C 17/32* (2013.01); *C07D 251/10* (2013.01); *C07D 251/34* (2013.01); *C07D 405/14* (2013.01); *C07F 7/1804* (2013.01); *C09D 5/00* (2013.01); *C23C 14/12* (2013.01); *C03C 2217/76* (2013.01); *C03C 2218/151* (2013.01)

(58) Field of Classification Search
None
See application file for complete search history.

(56) References Cited

U.S. PATENT DOCUMENTS

| 3,629,255 A | 12/1971 | Beyleveld et al. |
| 7,955,532 B2 | 6/2011 | Liang et al. |
| 8,609,742 B2 | 12/2013 | Wakita et al. |
| 8,828,565 B2 | 9/2014 | Sugiura et al. |
| 9,051,474 B2 | 6/2015 | Jung et al. |
| 10,125,107 B1 | 11/2018 | Miyamura et al. |
| 2004/0181008 A1 | 9/2004 | Hanazawa et al. |
| 2005/0121644 A1 | 6/2005 | Dams et al. |
| 2011/0000816 A1 | 1/2011 | Kato et al. |
| 2011/0065045 A1 | 3/2011 | Qiu et al. |
| 2012/0156510 A1 | 6/2012 | Okafuji et al. |
| 2012/0231297 A1 | 9/2012 | Sugiura et al. |
| 2013/0084458 A1 | 4/2013 | Yamada et al. |
| 2013/0345040 A1* | 12/2013 | Lee .......................... C03C 3/091 501/66 |
| 2015/0093561 A1* | 4/2015 | Tokunaga ............... C03C 3/091 428/220 |
| 2016/0002488 A1 | 1/2016 | Takao et al. |
| 2016/0237199 A1 | 8/2016 | Yoshida et al. |
| 2020/0024241 A1 | 1/2020 | Yamashita et al. |
| 2020/0095433 A1 | 3/2020 | Mitsuhashi et al. |
| 2020/0157376 A1 | 5/2020 | Hoshino et al. |

FOREIGN PATENT DOCUMENTS

| CN | 105658699 A | 6/2016 |
| CN | 106432686 A | 2/2017 |
| JP | 2005-047880 A | 2/2005 |
| JP | 2010-260193 A | 11/2010 |
| JP | 2011-518231 A | 6/2011 |
| JP | 2012-184339 A | 9/2012 |
| JP | 2012-207169 A | 10/2012 |
| JP | 2014-024288 A | 2/2014 |
| JP | 2014-218444 A | 11/2014 |
| JP | 2014-218548 A | 11/2014 |
| JP | 6182291 B1 | 8/2017 |
| KR | 10-2014-0018556 A | 2/2014 |

(Continued)

OTHER PUBLICATIONS

International Search Report for PCT/JP2017/034376 dated Nov. 28, 2017 [PCT/ISA/210].

(Continued)

*Primary Examiner* — Ramsey Zacharia
(74) *Attorney, Agent, or Firm* — Sughrue Mion, PLLC

(57) ABSTRACT

The invention aims to provide a substrate whose water-repellency is less likely to be deteriorated even after long-term use in an ultraviolet-exposure environment. The substrate of the invention includes a surface-treating layer, and exhibits a static contact angle with water of 100 degrees or greater after a 400-hour accelerated weathering test performed under the following conditions:

<conditions of accelerated weathering test> preparing a UVB-313 lamp exhibiting an irradiance of 0.63 W/m² at a wavelength of 310 nm; placing the surface-treating layer of the substrate apart from the lamp by 5 cm; and after every 24-hour irradiation, wiping the surface-treating layer with a cloth impregnated with water and with a cloth impregnated with ethanol, followed by drying.

6 Claims, No Drawings

(56) References Cited

FOREIGN PATENT DOCUMENTS

WO 03/002628 A1 1/2003
WO 2014/025716 A1 2/2014
WO 2015/056744 A1 4/2015

OTHER PUBLICATIONS

International Search Report for PCT/JP2017/034366 dated Dec. 26, 2017 [PCT/ISA/210].
Communication dated Feb. 20, 2020, from the European Patent Office in related European Application No. 17853181.0.
International Preliminary Report on Patentability with English Translation of Written Opinion dated Mar. 26, 2019 on PCT/JP2017/034376.
CAS Abstract and Indexed Compound US 2004/0181008 (2004) (total 25 pages).
Communication dated Dec. 10, 2019 from the U.S. Patent Office in co-pending U.S. Appl. No. 16/335,729.
Office Action dated Apr. 13, 2020 in related U.S. Appl. No. 16/335,729.
CAS Abstract and Additional Indexed Compounds, US 2004/0181008 (2004) (19 pages total).
CAS Abstract and Indexed Compounds U.S. Pat. No. 7955532 (2011) (2 pages total).
CAS Abstract and Indexed Compound JP 2005047880 (2005) (2 pages total).
Final Office Action dated Aug. 10, 2020 issued by the USPTO in U.S. Appl. No. 16/335,729.
CAS Abstract T. Hoshino et al., US 2020/015376 (2020).
English Language Machine Translation of Japanese Application No. 2017-159698 filed Aug. 22, 2017.
International Preliminary Report on Patentability with a Translation of Written Opinion in International Application No. PCT/JP2017/034366 dated Mar. 26, 2019.
Extended European Search Report dated Jun. 5, 2020, from the European Patent Office in Application No. 17853178.6.
Notice of Allowance dated Dec. 8, 2020 in related U.S. Appl. No. 16/335,729.

\* cited by examiner

WATER-REPELLENT SUBSTRATE

CROSS REFERENCE TO RELATED APPLICATIONS

This application is a National Stage of International Application No. PCT/JP2017/034366, filed on Sep. 22, 2017, which claims priority from Japanese Patent Application No. 2016-185759, filed on Sep. 23, 2016, Japanese Patent Application No. 2017-083841, filed on Apr. 20, 2017, Japanese Patent Application No. 2017-116961, filed on Jun. 14, 2017, and Japanese Patent Application No. 2017-149207, filed on Aug. 1, 2017.

TECHNICAL FIELD

The invention relates to water-repellent substrates.

BACKGROUND ART

Known water-repellent substrates include the following.

Patent Literature 1 discloses a kit for imparting water-repellency to a surface of a substrate.

The kit contains a coating composition (A) that essentially contains: a) at least one perfluoroalkyl trichlorosilane selected from compounds represented by the following formula:

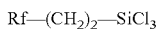

wherein Rf is a perfluoroalkyl radical group containing 3 to 18 alkyl carbon atoms; b) a perfluoropolyether carboxylic acid; and c) at least one fluorinated solvent.

Patent Literature 2 discloses a method for producing a water-repellent article including a water-repellent layer on a substrate. The method for producing a water-repellent article includes forming the water-repellent layer by applying, on the substrate, a liquid that contains a water-repellent compound containing a reactive silyl group having a weight average molecular weight of 1000 or greater and a liquid that contains a water-repellent compound containing a reactive silyl group having a weight average molecular weight of smaller than 1000 in the given order.

Patent Literature 3 discloses a substrate provided with a water-repellent film, including the substrate and the water-repellent film that is on at least part of a main surface of the substrate. The water-repellent film includes an intermediate layer and an outermost layer in the given order from the substrate side. The intermediate layer is formed from a coating composition for an intermediate layer, containing, as a main component of the whole solids content, a fluorine-containing silane compound (a) that is a hydrolyzable silane compound represented by the following formula (a1) and/or a partially hydrolyzed condensate thereof. The outermost layer is formed from a coating composition for an outermost layer, containing a fluorine-containing silane compound (b) in an amount of 70% by mass or more of the whole solids content, the fluorine-containing silane compound (b) being a hydrolyzable silane compound containing a perfluoropolyether group whose terminal perfluoroalkyl group has 1 to 6 carbon atoms and/or a partially hydrolyzed condensate thereof.

The symbols in the formula (a1) mean as follows:

$R^{F1}$: a C1-C6 perfluoroalkyl group containing no etheric oxygen atom between carbon atoms;

$Q^1$: a C1-C6 divalent organic group containing no fluorine atom;

$X^1$: a C1-C10 alkoxy group, a C2-C10 oxyalkoxy group, a C2-C10 acyloxy group, a C2-C10 alkenyloxy group, a halogen atom, or an isocyanate group, with m1 $X^1$s being the same as or different from each other;

$R^1$: a hydrogen atom or a C1-C8 monovalent hydrocarbon group containing no fluorine atom and with any or all of hydrogen atoms being optionally substituted, with 3-m1 $R^1$s being the same as or different from each other; and m1: an integer of 1 to 3.

CITATION LIST

Patent Literature

Patent Literature 1: JP 2011-518231 T
Patent Literature 2: JP 2010-260193 A
Patent Literature 3: JP 2014-024288 A

SUMMARY OF INVENTION

Technical Problem

Unfortunately, conventional water-repellent substrates have insufficient durability against ultraviolet light and the water-repellency thereof is deteriorated when the substrates are continuously used outside.

In view of the above current state of the art, the invention aims to provide a substrate whose water-repellency is less likely to be deteriorated even after long-term use in an ultraviolet-exposure environment. In other words, the invention aims to maintain the antifouling property for a long period of time even after long-term use in an ultraviolet-exposure environment.

Solution to Problem

The invention relates to a substrate (hereinafter, also referred to as a "first substrate") including a surface-treating layer and exhibiting a static contact angle with water of 100 degrees or greater after a 400-hour accelerated weathering test performed under the following conditions:

<conditions of accelerated weathering test> preparing a UVB-313 lamp exhibiting an irradiance of 0.63 W/m² at a wavelength of 310 nm; placing the surface-treating layer of the substrate apart from the lamp by 5 cm; and after every 24-hour irradiation, wiping the surface-treating layer with a cloth impregnated with water and with a cloth impregnated with ethanol, followed by drying.

The invention also relates to a substrate (hereinafter, also referred to as a "second substrate") including a surface-treating layer and exhibiting a static contact angle with water of 110 degrees or greater after a 250-hour accelerated weathering test performed under the following conditions:

<conditions of accelerated weathering test> preparing a UVB-313 lamp exhibiting an irradiance of 0.63 W/m² at a wavelength of 310 nm; placing the surface-treating layer of the substrate apart from the lamp by 5 cm; and after every 24-hour irradiation, wiping the surface-treating layer with a cloth impregnated with water and with a cloth impregnated with ethanol, followed by drying.

The first and second substrates of the invention preferably exhibit a static contact angle with water of 100 degrees or greater after 6000 processes of steel wool friction durability evaluation performed under the following conditions:

<conditions of steel wool friction durability evaluation> bringing #0000-grade steel wool having dimensions of 5 mm×10 mm×10 mm into contact with the surface-treating layer of the substrate; applying a load of 1000 gf thereto; and reciprocating the steel wool at a rate of 140 mm/sec with the load, where one reciprocating motion is counted as one process.

The invention also relates to a substrate (hereinafter, also referred to as a "third substrate") including a surface-treating layer, the surface-treating layer containing a compound represented by the following formula (1):

[Chem. 1]

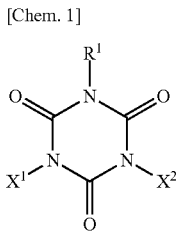

wherein $R^1$ is a monovalent organic group represented by $R^3$—$(OR^2)_a$-L-, wherein $(OR^2)_a$ is a polyether chain; $R^3$ is an alkyl group or a fluorinated alkyl group; and L is a single bond or a divalent linking group;

$X^1$ is a monovalent Si-containing group; and $X^2$ is a monovalent group, the polyether chain being a chain represented by the following formula:

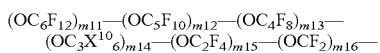

wherein m11, m12, m13, m14, m15, and m16 are each independently an integer of 0 or 1 or greater;

$X^{10}$s are each independently H, F, or Cl; and the repeating units are present in any order.

L is preferably —$C_2H_4$—, —$C_3H_6$—, —CO—O—$CH_2$—CH(OH)—$CH_2$—, —$(CF_2)_n$—, wherein n is an integer of 0 to 4, —$CH_2$—, —$C_4H_8$—, or —$(CF_2)_n$—$(CH_2)_m$—, wherein n and m are each independently an integer of 0 to 4; and $X^1$ is preferably a monovalent Si-containing group containing a hydrolyzable group.

The substrate is preferably a glass substrate.

The glass substrate is preferably a sapphire glass substrate, a soda-lime glass substrate, an alkali aluminum silicate glass substrate, a borosilicate glass substrate, an alkali-free glass substrate, a lead glass substrate, or a quartz glass substrate.

Advantageous Effects of Invention

The substrates of the invention exhibit water-repellency that is less likely to be deteriorated even after long-term use in an ultraviolet-exposure environment. In other words, the antifouling property thereof is less likely to be deteriorated.

DESCRIPTION OF EMBODIMENTS

The invention will be specifically described hereinbelow.

The first substrate of the invention includes a surface-treating layer and exhibits a static contact angle with water of 100 degrees or greater after a 400-hour accelerated weathering test performed under specific conditions. The static contact angle with water is preferably 105 degrees or greater, and may be 120 degrees or smaller. The static contact angle with water is determined with 2 µL of water using a contact angle meter (Kyowa Interface Science Co., Ltd.). The static contact angle with water is the static contact angle with water of the surface-treating layer.

The second substrate of the invention includes a surface-treating layer and exhibits a static contact angle with water of 110 degrees or greater after a 250-hour accelerated weathering test performed under specific conditions.

The accelerated weathering test is performed as follows: a UVB-313 lamp (Q-Lab Corp., irradiance at a wavelength of 310 nm: 0.63 W/m$^2$) is prepared; the surface-treating layer of the substrate is placed apart from the lamp by 5 cm; and after every 24-hour irradiation, the surface-treating layer is wiped with a cloth impregnated with water and with a cloth impregnated with ethanol, and then dried.

The duration of the accelerated weathering test is preferably 408 hours, more preferably 250 hours.

In order to achieve excellent abrasion resistance, the first and second substrates of the invention preferably exhibit a static contact angle with water of 100 degrees or greater after 6000 processes of steel wool friction durability evaluation performed under specific conditions. The static contact angle with water is preferably 100 degrees or greater, and may be 120 degrees or smaller. The static contact angle with water is determined with 2 µL of water using a contact angle meter (Kyowa Interface Science Co., Ltd.).

The steel wool friction durability evaluation is performed as follows: steel wool (grade: #0000, dimensions: 5 mm×10 mm×10 mm) is brought into contact with the surface-treating layer of the substrate; a load of 1000 gf is applied thereto; and the steel wool is reciprocated at a rate of 140 mm/sec with the load, where one reciprocating motion is counted as one process. The static contact angle with water is the static contact angle with water of the surface-treating layer.

The substrates of the invention each may be formed of any appropriate material such as glass, metal, resin, a metal oxide such as ceramic, a semiconductor (e.g., silicon, germanium), fiber (e.g., woven fabric, nonwoven fabric), fur, leather, wood, stone, ceramic ware, or a building material. Preferred among these is a glass substrate because it has excellent transparency and can maintain excellent water-repellency for a long period of time.

Examples of the glass substrate include inorganic glass substrates; organic glass substrates; alkali-containing glass substrates such as alkali aluminum silicate glass substrates and soda-lime glass substrates; alkali-free glass substrates such as borosilicate glass substrates; sapphire glass substrates; lead glass substrates; and quartz glass substrates. The glass substrate may contain a functional group such as a hydroxy group, an amino group, or a thiol group on a surface thereof. The glass substrate may be a laminated glass or a reinforced glass, for example. The glass substrate is preferably a sapphire glass substrate, a soda-lime glass substrate, an alkali aluminum silicate glass substrate, a borosilicate glass substrate, an alkali-free glass substrate, a lead glass substrate, or a quartz glass substrate.

Examples of the metal include iron, copper, aluminum, stainless steel, nickel, chromium, and molybdenum. The metal may be a simple metal or a composite such as an alloy thereof.

Examples of the resin include cellulose resins such as triacetyl cellulose (TAC), polyolefins such as polyethylene, polypropylene, ethylene-propylene copolymers, and ethylene-vinyl acetate copolymers (EVA), cyclic polyolefins, modified polyolefins, polyvinyl chloride, polyvinylidene chloride, polystyrene, polyamide, polyimide, polyamide-imide, polycarbonate, poly-(4-methyl pentene-1), ionomers, acrylic resin, polymethyl methacrylate, acryl-styrene copolymers (AS resin), butadiene-styrene copolymers, ethylene-vinyl alcohol copolymers (EVOH), polyesters such as polyethylene terephthalate (PET), polybutylene terephthalate (PBT), and polycyclohexane terephthalate (PCT), polyether, polyether ketone (PEK), polyether ether ketone (PEEK), polyetherimide, polyacetal (POM), polyphenylene oxide, modified polyphenylene oxide, polyarylate, aromatic polyester (liquid crystal polymers), polytetrafluoroethylene, polyvinylidene fluoride, other fluororesins, styrene-, polyolefin-, polyvinyl chloride-, polyurethane-, fluororubber-, or chlorinated polyethylene-based thermoplastic elastomers, epoxy resin, phenol resin, urea resin, melamine resin, unsaturated polyester, silicone resin, and polyurethane, and copolymers, blends, and polymer alloys mainly formed from these polymers. One of these may be used or two or more of these may be used in combination (for example, in the form of a laminate of two or more layers).

For the substrates of the invention which are optical members, for example, the surface of each substrate may be formed from a material for an optical member, such as glass or transparent plastic. For the substrates of the invention which are optical members, the surface (outermost layer) of each substrate may be covered with a certain layer (or film) such as a hard coating layer or an antireflection layer. The antireflection layer may be either a monolayered antireflection layer or a multilayered antireflection layer. Examples of an inorganic substance to be used for the antireflection layer include $SiO_2$, $SiO$, $ZrO_2$, $TiO_2$, $TiO$, $Ti_2O_3$, $Ti_2O_5$, $Al_2O_3$, $Ta_2O_5$, $CeO_2$, $MgO$, $Y_2O_3$, $SnO_2$, and $WO_3$. These inorganic substances may be used alone, or may be used in combination of two or more (for example, in the form of a mixture). In the case of a multilayered antireflection layer, the outermost layer thereof is preferably formed from $SiO_2$ and/or $SiO$. For the substrates of the invention which are optical glass members for touchscreens, part of the surface of each substrate (glass) may be provided with a transparent electrode, such as a thin film formed of indium tin oxide (ITO) or indium zinc oxide. In accordance with the specifications thereof, the substrate, may be provided with any of an insulating layer, an adhesive layer, a protecting layer, a decorated frame layer (I-CON), a sprayed layer, a hard coating layer, a polarizing film, a retardation film, a liquid crystal display module, and the like. Similarly, for the substrates of the invention which are optical lens members such as onboard cameras or cameras for monitors, the inorganic substances to be used for the antireflection layer may be used alone, or may be used in combination of two or more. The antireflection layer has a thickness within the range of 0.001 to 1.0 µm, preferably 0.01 to 0.2 µm.

The substrates may have any shape. A surface region to be provided with the surface-treating layer of each substrate may be at least part of the substrate surface and may be determined in accordance with factors such as the use and specifications of the substrate of the invention. The surface-treating layer is preferably present on the outermost surface.

The substrates, or at least the surface portion thereof, each may be formed from a material originally containing a hydroxy group. The material may be glass, or may be metal (especially a base metal), ceramic, or a semiconductor on a surface of which a natural oxidized film or a thermal oxidized film is formed. Alternatively, if the material contains a hydroxy group in an insufficient amount, such as resin, or originally contains no hydroxy group, the substrate may be subjected to a certain pretreatment so that a hydroxy group is introduced to the surface of the substrate or the amount thereof is increased. Examples of the pretreatment include plasma treatment (e.g., corona discharge) and ion beam irradiation. Plasma treatment may suitably be used not only for introducing a hydroxy group to the substrate surface or increasing the amount thereof, but also for cleaning the substrate surface (removing foreign substances, for example). Another example of the pretreatment is a method in which a unimolecular film of an interface adsorbing agent containing a carbon-carbon unsaturated bond group is formed in advance on the substrate surface by the Langmuir-Blodgett (LB) method or chemisorption, and then the unsaturated bond is cleaved in an atmosphere containing, for example, oxygen and nitrogen.

Still alternatively, the substrate, or at least the surface portion thereof, may be formed from a silicone compound containing one or more different reactive groups, such as Si—H groups, or a material containing an alkoxysilane.

The surface-treating layer preferably contains a compound represented by the following formula (1):

[Chem. 2]

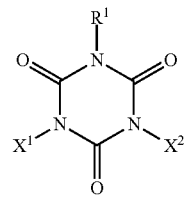

wherein $R^1$ is a monovalent organic group represented by $R^3$—$(OR^2)_a$-L-, wherein $(OR^2)^a$ is a polyether chain; $R^3$ is an alkyl group or a fluorinated alkyl group; and L is a single bond or a divalent linking group; $X^1$ is a monovalent Si-containing group, and $X^2$ is a monovalent group, the polyether chain being a chain represented by the following formula:

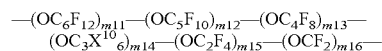

wherein m11, m12, m13, m14, m15, and m16 are each independently an integer of 0 or 1 or greater; $X^{10}$s are each independently H, F, or Cl; and the repeating units are present in any order.

The third substrate of the invention includes a surface-treating layer, and the surface-treating layer contains a compound represented by the formula (1).

The inventors performed studies to surprisingly find that the surface-treating layer containing a compound represented by the formula (1) can impart to the substrate a function of reducing deterioration of the water-repellency even after long-term use in an ultraviolet-exposure environment. This is presumably because as follows. That is, the polyether chain imparts water-repellency, the monovalent Si-containing group enables firm bonding of the compound to the substrate, and the polyether chain and the monovalent Si-containing group are firmly linked via an isocyanuric skeleton. Thereby, even when ultraviolet light is incident, the surface-treating layer is neither decomposed nor separated from the substrate, and the water-repellency is maintained for a long period of time.

$X^1$ is preferably a monovalent Si-containing group containing a hydrolyzable group.

The "hydrolyzable group" as used herein means a group that can be separated from the main skeleton of the compound in response to a hydrolysis reaction. Examples of the hydrolyzable group include —OR, —OCOR, —O—N=CR$_2$, —NR$_2$, —NHR, and halogens, wherein R is a substituted or unsubstituted C1-C4 alkyl group. Preferred is —OR (i.e., an alkoxy group). Examples of R include unsubstituted alkyl groups such as a methyl group, an ethyl group, a propyl group, an isopropyl group, a n-butyl group, an isobutyl group; and substituted alkyl groups such as a chloromethyl group. Preferred among these are alkyl groups, especially unsubstituted alkyl groups, more preferred is a methyl group or an ethyl group.

$X^2$ may be a monovalent organic group containing a polyether chain, a monovalent Si-containing group, an acryloyl group, a methacryloyl group, an epoxy group, a glycidyl group, an oxetane group, an isocyanate group, a vinyl group, an allyl group, a vinyloxy group, a carboxyl group, a mercapto group, an amino group, a hydroxy group, a phosphonyl group, a cyclic acid anhydride group, a lactone group, a lactam group, a —OC(O)Cl group, a triazine group, an imidazole group, a conjugated olefin group, an acetylene group, a diazo group, an aldehyde group, a ketone group, an alkyl boron group, an alkyl aluminum group, an alkyl tin group, an alkyl germanium group, an alkyl zircon group, H, an alkyl group, a halogenated alkyl group, an alkyl ester group, a halogenated alkyl ester group, an alkyl ether group, a halogenated alkyl ether group, an alkyl amide group, a halogenated alkyl amide group, an uril group, a halogenated uril group, a urea group, a halogenated urea group, —OCO—OR$^j$ (wherein R$^j$ is an alkyl group or a halogenated alkyl group), —CONR$^k$COR$^l$ (wherein R$^k$ and R$^l$ are each independently H, an alkyl group, or a halogenated alkyl group), a glycan-containing group, an alkylene polyether group, an arene group, a halogenated arene group, a hetero-ring-containing group, an aryl group, a halogenated aryl group, a silicone residue (other than those containing a reactive group), a silsesquioxane residue (other than those containing a reactive group), and a monovalent group containing any of these groups.

In particular, $X^2$ is preferably at least one selected from the group consisting of a monovalent organic group containing a polyether chain and a monovalent Si-containing group. In order to maintain excellent water-repellency for a long period of time, a monovalent Si-containing group is preferred. In this case, the monovalent Si-containing group of $X^1$ and the monovalent Si-containing group of $X^2$ may be the same as or different from each other. In order to produce the compound easily, they are preferably the same as each other.

$R^1$ is a monovalent organic group containing a polyether chain (other than those containing a urethane bond).

$X^{10}$ is preferably F.

Each of m11 to m16 is preferably an integer of 0 to 200, more preferably an integer of 0 to 100. The sum of m11 to m16 is preferably an integer of 1 or greater, more preferably an integer of 5 or greater, still more preferably an integer of 10 or greater. The sum of m11 to m16 is preferably an integer of 200 or smaller, more preferably an integer of 100 or smaller. The sum of m11 to m16 is preferably an integer of 10 to 200, more preferably an integer of 10 to 100.

Each repeating unit in the polyether chain may be linear or branched, and is preferably linear. For example, the repeating unit —(OC$_6$F$_{12}$)— may be —(OCF$_2$CF$_2$CF$_2$CF$_2$CF$_2$CF$_2$)—, —(OCF(CF$_3$)CF$_2$CF$_2$CF$_2$CF$_2$)—, —(OCF$_2$CF(CF$_3$)CF$_2$CF$_2$CF$_2$)—, —(OCF$_2$CF$_2$CF(CF$_3$)CF$_2$CF$_2$)—, —(OCF$_2$CF$_2$CF$_2$CF(CF$_3$)CF$_2$)—, or —(OCF$_2$CF$_2$CF$_2$CF$_2$CF(CF$_3$))—, and is preferably —(OCF$_2$CF$_2$CF$_2$CF$_2$CF$_2$CF$_2$)—. The repeating unit —(OC$_5$F$_{10}$)— may be —(OCF$_2$CF$_2$CF$_2$CF$_2$CF$_2$)—, —(OCF(CF$_3$)CF$_2$CF$_2$CF$_2$)—, —(OCF$_2$CF(CF$_3$)CF$_2$CF$_2$)—, —(OCF$_2$CF$_2$CF(CF$_3$)CF$_2$)—, or —(OCF$_2$CF$_2$CF$_2$CF(CF$_3$))—, and is preferably —(OCF$_2$CF$_2$CF$_2$CF$_2$CF$_2$)—. The repeating unit —(OC$_4$F$_8$)— may be any of —(OCF$_2$CF$_2$CF$_2$CF$_2$)—, —(OCF(CF$_3$)CF$_2$CF$_2$)—, —(OCF$_2$CF(CF$_3$)CF$_2$)—, —(OCF$_2$CF$_2$CF(CF$_3$))—, —(OC(CF$_3$)$_2$CF$_2$)—, —(OCF$_2$C(CF$_3$)$_2$)—, —(OCF(CF$_3$)CF(CF$_3$))—, —(OCF(C$_2$F$_5$)CF$_2$)—, and —(OCF$_2$CF(C$_2$F$_5$))—, and is preferably —(OCF$_2$CF$_2$CF$_2$CF$_2$)—. The repeating unit —(OC$_3$F$_6$)— may be any of —(OCF$_2$CF$_2$CF$_2$)—, —(OCF(CF$_3$)CF$_2$)—, and —(OCF$_2$CF(CF$_3$))—, and is preferably —(OCF$_2$CF$_2$CF$_2$)—. The repeating unit —(OC$_2$F$_4$)— may be any of —(OCF$_2$CF$_2$)— and —(OCF(CF$_3$))—, and is preferably —(OCF$_2$CF$_2$)—.

In an embodiment, the polyether chain is a chain represented by —(OC$_3$F$_6$)$_{m14}$— (wherein m14 is an integer of 1 to 200). The polyether chain is preferably a chain represented by —(OCF$_2$CF$_2$CF$_2$)$_{m14}$— (wherein m14 is an integer of 1 to 200) or a chain represented by —(OCF(CF$_3$)CF$_2$)$_{m14}$— (wherein m14 is an integer of 1 to 200), more preferably a chain represented by —(OCF$_2$CF$_2$CF$_2$)$_{m14}$— (wherein m14 is an integer of 1 to 200). In the formula, m14 is preferably an integer of 5 to 200, more preferably an integer of 10 to 200.

In another embodiment, the polyether chain is a chain represented by —(OC$_4$F$_8$)$_{m13}$—(OC$_3$F$_6$)$_{m14}$—(OC$_2$F$_4$)$_{m15}$—(OCF$_2$)$_{m16}$— (wherein m13 and m14 are each an integer of 0 to 30; m15 and m16 are each an integer of 1 to 200; the sum of m13 to m16 is an integer of 5 or greater; and the repeating units are present in any order). In the formula, m15 and m16 are each preferably an integer of 5 to 200, more preferably an integer of 10 to 200. The sum of m13 to m16 is preferably an integer of 10 or greater. The polyether chain is preferably —(OCF$_2$CF$_2$CF$_2$CF$_2$)$_{m13}$—(OCF$_2$CF$_2$CF$_2$)$_{m14}$—(OCF$_2$CF$_2$)$_{m15}$—(OCF$_2$)$_{m16}$—. In an embodiment, the polyether chain may be a chain represented by —(OC$_2$F$_4$)$_{m15}$—(OCF$_2$)$_{m16}$— (wherein m15 and m16 are each an integer of 1 to 200; and the repeating units are present in any order). In the formula, m15 and m16 are each preferably an integer of 5 to 200, more preferably an integer of 10 to 200.

In still another embodiment, the polyether chain is a group represented by —(R$^{m1}$—R$^{m2}$)$_{m17}$—. In the formula, R$^{m1}$ is OCF$_2$ or OC$_2$F$_4$, preferably OC$_2$F$_4$. In the formula, R$^{m2}$ is a group selected from OC$_2$F$_4$, OC$_3$F$_6$, OC$_4$F$_8$, OC$_5$F$_{10}$, and OC$_6$F$_{12}$, or any combination of two or three groups individually selected from these groups. Preferably, R$^{m1}$ is a group selected from OC$_2$F$_4$, OC$_3$F$_6$, and OC$_4$F$_8$, a group selected from OC$_3$F$_6$, OC$_4$F$_8$, OC$_5$F$_{10}$, and OC$_6$F$_{12}$, or any combination of two or three groups individually selected from these groups. Examples of the combination of two or three groups individually selected from OC$_2$F$_4$, OC$_3$F$_6$, and OC$_4$F$_8$ include, but are not limited to, —OC$_2$F$_4$OC$_3$F$_6$—, —OC$_2$F$_4$OC$_4$F$_8$—, —OC$_3$F$_6$OC$_2$F$_4$—, —OC$_3$F$_6$OC$_3$F$_6$—, —OC$_3$F$_6$OC$_4$F$_8$—, —OC$_4$F$_8$OC$_4$F$_8$—, —OC$_4$F$_8$OC$_3$F$_6$—, —OC$_4$F$_8$OC$_2$F$_4$—, —OC$_2$F$_4$OC$_2$F$_4$OC$_3$F$_6$—, —OC$_2$F$_4$OC$_2$F$_4$OC$_4$F$_8$—, —OC$_2$F$_4$OC$_3$F$_6$OC$_2$F$_4$—, —OC$_2$F$_4$OC$_3$F$_6$OC$_3$F$_6$—, —OC$_2$F$_4$OC$_4$F$_8$OC$_2$F$_4$—, —OC$_3$F$_6$OC$_2$F$_4$OC$_2$F$_4$—, —OC$_3$F$_6$C$_2$F$_4$O$_3$F$_6$—, —OC$_3$F$_6$OC$_3$F$_6$OC$_3$F$_6$OC$_2$F$_4$—, and —OC$_4$F$_8$OC$_2$F$_4$OC$_2$F$_4$—. In the formula, m17 is an integer of 2 or greater, preferably an integer of 3 or greater, more preferably an integer of 5 or greater, while an integer of 100 or smaller, preferably an integer of 50 or smaller. In the formula, OC$_2$F$_4$, OC$_3$F$_6$, OC$_4$F, OC$_5$F$_{10}$, and OC$_6$F$_{12}$ each may be linear or branched, and is preferably linear. In this embodiment, the polyether chain is preferably —(OC$_2$F$_4$—OC$_3$F$_6$)$_{m17}$— or —(OC$_2$F$_4$—OC$_4$F$_8$)$_{m17}$—.

In the polyether chain, the ratio of m15 to m16 (hereinafter, referred to as the "m15/m16 ratio") may be 0.1 to 10, preferably 0.2 to 5, more preferably 0.2 to 2, still more preferably 0.2 to 1.5, further more preferably 0.2 to 0.85. The polyether chain having an m15/m16 ratio of 10 or lower can lead to more improved lubricity, friction durability, and chemical resistance (e.g., durability against artificial sweat) of the surface-treating layer. The lower the m15/m16 ratio is, the more the lubricity and friction durability of the surface-treating layer are improved. The polyether chain having an m15/m16 ratio of 0.1 or higher can lead to much better stability of the compound. The higher the m15/m16 ratio is, the more the stability of the compound is improved.

The polyether chain may be at least one chain selected from the group consisting of:

a chain represented by the following formula:

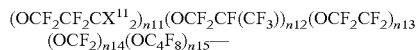
(OCF$_2$CF$_2$CX$^{11}$$_2$)$_{n11}$(OCF$_2$CF(CF$_3$))$_{n12}$(OCF$_2$CF$_2$)$_{n13}$(OCF$_2$)$_{n14}$(OC$_4$F$_8$)$_{n15}$— wherein n11, n12, n13, n14, and n15 are each independently an integer of 0 or 1 or greater; X$^{11}$s are each independently H, F, or Cl; and the repeating units are present in any order; and a chain represented by the following formula:

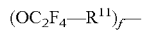
(OC$_2$F$_4$—R$^{11}$)$_f$— wherein R$^{11}$ is a group selected from OC$_2$F$_4$, OC$_3$F$_6$, and OC$_4$F$_8$; and f is an integer of 2 to 100.

X$^{11}$ is preferably F.

In the formula, n11 to n15 are each preferably an integer of 0 to 200. The sum of n11 to n15 is preferably an integer of 2 or greater, more preferably an integer of 5 to 300, still more preferably an integer of 10 to 200, particularly preferably an integer of 10 to 100.

R$^{11}$ is a group selected from OC$_2$F$_4$, OC$_3$F$_6$, and OC$_4$F$_8$, or any combination of two or three groups individually selected from these groups. Examples of the combination of two or three groups individually selected from OC$_2$F$_4$, OC$_3$F$_6$, and OC$_4$F$_8$ include, but are not limited to, —OC$_2$F$_4$OC$_3$F$_6$—, —OC$_2$F$_4$OC$_4$F$_8$—, —OC$_3$F$_6$OC$_2$F$_4$—, —OC$_3$F$_6$OC$_3$F$_6$—, —OC$_3$F$_6$OC$_4$F$_8$—, —OC$_4$F$_8$OC$_4$F$_8$—, —OC$_4$F$_8$OC$_3$F$_6$—, —OC$_4$F$_8$OC$_2$F$_4$—, —OC$_2$F$_4$OC$_2$F$_4$OC$_3$F$_6$—, —OC$_2$F$_4$OC$_2$F$_4$OC$_4$F$_8$—, —OC$_2$F$_4$OC$_3$F$_6$OC$_2$F$_4$—, —OC$_2$F$_4$OC$_3$F$_6$OC$_3$F$_6$—, —OC$_2$F$_4$OC$_4$F$_8$OC$_2$F$_4$—, —OC$_3$F$_6$OC$_2$F$_4$OC$_2$F$_4$—, —OC$_3$F$_6$OC$_2$F$_4$OC$_3$F$_6$—, —OC$_3$F$_6$OC$_3$F$_6$OC$_2$F$_4$—, and —OC$_4$F$_8$OC$_2$F$_4$OC$_2$F$_4$—. In the formula, f is an integer of 2 to 100, preferably an integer of 2 to 50. In the formula, OC$_2$F$_4$, OC$_3$F$_6$, and OC$_4$F$_8$ each may be linear or branched, and is preferably linear. In this embodiment, —(OC$_2$F$_4$—R$^{11}$)$_f$— is preferably —(OC$_2$F$_4$—OC$_3$F$_6$)$_f$— or —(OC$_2$F$_4$—OC$_4$F$_8$)$_f$—.

In the compound represented by the formula (1), the polyether chain moiety has a number average molecular weight of, for example, 500 to 30000, preferably 1500 to 30000, more preferably 2000 to 10000, although not limited thereto. The number average molecular weight is a value determined by $^{19}$F-NMR.

In another embodiment, the number average molecular weight of the polyether chain moiety is 500 to 30000, preferably 1000 to 20000, more preferably 2000 to 15000, still more preferably 2000 to 10000, and may be 3000 to 6000.

In another embodiment, the number average molecular weight of the polyether chain moiety may be 4000 to 30000, preferably 5000 to 10000, more preferably 6000 to 10000.

R$^3$ preferably contains 1 to 16, more preferably 1 to 8 carbon atoms.

R$^3$ may be linear or branched, and is preferably a linear or branched C1-C16 alkyl or fluorinated alkyl group, more preferably a linear or branched C1-C8 alkyl or fluorinated alkyl group, still more preferably a linear or branched C1-C6 alkyl or fluorinated alkyl group, further more preferably a linear or branched C1-C3 alkyl or fluorinated alkyl group, particularly preferably a linear C1-C3 alkyl or fluorinated alkyl group.

R$^3$ is preferably a C1-C16 fluorinated alkyl group, more preferably a CF$_2$H—C$_{1-15}$ fluoroalkylene group or a C1-C16 perfluoroalkyl group, still more preferably a C1-C16 perfluoroalkyl group.

The C1-C16 perfluoroalkyl group may be linear or branched, and is preferably a linear or branched C1-C6, particularly C1-C3, perfluoroalkyl group, more preferably a linear C1-C3 perfluoroalkyl group, specifically —CF$_3$, —CF$_2$CF$_3$, or —CF$_2$CF$_2$CF$_3$.

L is a single bond or a divalent linking group that directly binds to the ring in the formula (1). L is preferably a single bond, an alkylene group, or a divalent group containing an ester bond, more preferably a single bond, a C1-C10 alkylene group, or a C1-C10 divalent hydrocarbon group containing an ester bond.

L is still more preferably a group represented by the following formula:

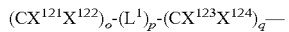
(CX$^{121}$X$^{122}$)$_o$-(L$^1$)$_p$-(CX$^{123}$X$^{124}$)$_q$— wherein X$^{121}$ to X$^{124}$ are each independently H, F, OH, or —OSi(OR$^{121}$)$_3$ (wherein three R$^{121}$s are each independently a C1-C4 alkyl group); L$^1$ is —C(=O)O— or —NHC(=O)NH— (wherein the left side of each bond binds to CX$^{121}$X$^{122}$); o is an integer of 0 to 10; p is 0 or 1; and q is an integer of 1 to 10.

L is particularly preferably a group represented by the following formula:

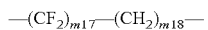
—(CF$_2$)$_{m17}$—(CH$_2$)$_{m18}$— wherein m17 is an integer of 1 to 3; and m18 is an integer of 1 to 3.

Specific examples of L include —C$_2$H$_4$—, —C$_3$H$_6$—, —CO—O—CH$_2$—CH(OH)—CH$_2$—, —(CF$_2$)$_n$— (wherein n is an integer of 0 to 4), —CH$_2$—, —C$_4$H$_8$—, and —(CF$_2$)$_n$—(CH$_2$)$_m$— (wherein n and m are each independently an integer of 0 to 4). L is preferably —C$_2$H$_4$—, —C$_3$H$_6$—, —CO—O—CH$_2$—CH(OH)—CH$_2$—, —(CF$_2$)$_n$— (wherein n is an integer of 0 to 4), —CH$_2$—, —C$_4$H$_8$—, or —(CF$_2$)$_n$—(CH$_2$)$_m$— (wherein n and m are each independently an integer of 0 to 4).

The Si-containing group is preferably at least one group selected from the group consisting of a silane-containing reactive crosslinkable group, a silicone residue, a silsesquioxane residue, and a silazane group.

In order to maintain excellent water-repellency for a long period of time, the Si-containing group is preferably at least one selected from the group consisting of -L$^2$-SiR$^5$$_3$, -L$^2$-Si(OR$^6$)$_3$, -L$^2$-Si(NR$^6$$_2$)$_3$, and -L$^2$-Si(OCOR$^6$)$_3$ wherein L$^2$ is a single bond or a divalent linking group; R$^5$ is a halogen atom; and R$^6$s are each independently a C1-C4 alkyl group. More preferred is -L$^2$-Si(OR$^6$)$_3$, wherein L$^2$ is a single bond or a divalent linking group; and R$^6$s are each independently a C1-C4 alkyl group.

The silane-containing reactive crosslinkable group is preferably a group represented by the following formula:

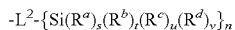
-L$^2$-{Si(R$^a$)$_s$(R$^b$)$_t$(R$^c$)$_u$(R$^d$)$_v$}$_n$ (wherein $L^2$ is a single bond or a divalent linking group; $R^a$, $R^b$, and $R^c$ are the same as or different from each other, and are each hydrogen, a halogen, a C1-C10 alkoxy group, a C1-C10 amino group, a C1-C10 acetoxy group, a C3-C10 allyl group, or a C3-C10 glycidyl group; $R^d$s are the same as or different from each other, and are each —O—, —NH—, —C≡C—, or a silane bond; s, t, and u are the same as or different from each other, and are each 0 or 1; v is an integer of 0 to 3; n is an integer of 1 to 20; when n is 1, (s+t+u) is 3 and v is 0; when n is 2 to 20, the (s+t+u) values are the same as or different from each other and are each 0 to 2, and vs are the same as or different from each other and are each 0 to 2; and when v is an integer of 1 or greater, at least two Si atoms are bound to each other via $R^d$ in the form of a straight chain, a ladder, a cycle, or a polycycle). $R^a$, $R^b$, and $R^c$ are each a monovalent group binding to Si. $R^d$ is a divalent group binding to two Si atoms.

$R^a$, $R^b$, and $R^c$ are the same as or different from each other. At least one thereof is hydrogen, a halogen, a C1-C10 alkoxy group, or a C1-C10 amino group, while the others thereof are each preferably a C1-C10 acetoxy group, a C3-C10 allyl group, or a C3-C10 glycidyl group, still more preferably a C1-C4 alkoxy group. When n is 2 to 20, preferably, the (s+t+u) values are the same as or different from each other and are each 0 to 2, and v is 0 to 2.

In $R^a$, $R^b$, and $R^c$, the halogen is preferably Cl, Br, or I, more preferably Cl.

In $R^a$, $R^b$, and $R^c$, the alkoxy group preferably contains 1 to 5 carbon atoms. The alkoxy group may be linear, cyclic, or branched. Any of the hydrogen atoms may be replaced by a different atom such as a fluorine atom. The alkoxy group is preferably a methoxy group, an ethoxy group, a propyloxy group, or a butoxy group, more preferably a methoxy group or an ethoxy group.

$R^d$s are the same as or different from each other, and are each —O—, —NH—, —C≡C—, or a silane bond. $R^d$s are each preferably —O—, —NH—, or —C≡C—. $R^d$s are each a divalent group binding to two Si atoms, and $R^d$ allows two or more silicon atoms to bind to each other via $R^d$ in the form of a straight chain, a ladder, a cycle, or a polycycle. When n is an integer of 2 or greater, the silicon atoms themselves may bind to each other.

$R^d$s are the same as or different from each other, and each may be a group represented by —Z—SiR$^{d1}_p$R$^{d2}_q$R$^{d3}_r$—.

In the formula, Zs are the same as or different from each other, and are each a single bond or a divalent linking group. Specific examples of Z include —$C_2H_4$—, —$C_3H_6$—, —CO—O—$CH_2$—CH(OH)—$CH_2$—, —$CH_2$—, and —$C_4H_8$—.

In the formula, $R^{d1}$s are the same as or different from each other; and are each $R^{d'}$. $R^{d'}$ is defined in the same manner as $R^d$.

The number of Si atoms linearly linked via the Z group in $R^d$ is at most five. In other words, when at least one $R^{d1}$ is present in $R^d$, there are two or more Si atoms linearly linked via the Z group in $R^d$, and the number of Si atoms linearly linked via such a Z group is at most five. The "number of Si atoms linearly linked via the Z group in $R^d$" is equivalent to the number of repeated —Z—Si— units linearly linked in $R^d$.

An example of linking of Si atoms via the Z group in $R^d$ is shown below.

[Chem. 3]

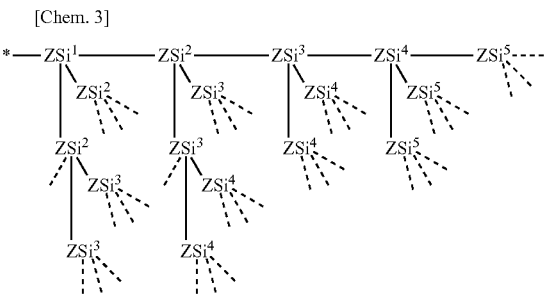

In the formula, the symbol * represents the site binding to Si in the main chain; and the symbol . . . represents binding of a predetermined group other than ZSi. In other words, when all of the three bindings of a Si atom are represented by the symbol . . . , it means the site where repeat of ZSi is finished. The superscript immediately after Si is the occurrence number of Si atoms linearly linked from the symbol * via the Z group. In other words, when the ZSi repeating is finished at $Si^2$, the chain is considered as including two "Si atoms linearly linked via the Z group in $R^d$". Similarly, when ZSi repeating is finished at $Si^3$, $Si^4$, and $Si^5$, the chain includes three, four, and five "Si atoms linearly linked via the Z group in $R^d$", respectively. As is clear from the above formula, a plurality of ZSi chains is present in $R^d$. Still, they need not to be the same length, and may have the respective lengths.

In a preferred embodiment, as shown below, the "number of Si atoms linearly linked via the Z group in $R^d$" is one (left formula) or two (right formula) in all the chains.

[Chem. 4]

In an embodiment, the number of Si atoms linearly linked via the Z group in $R^d$ is one or two, preferably one.

In the formula, $R^{d2}$s are the same as or different from each other, and are each a hydroxy group or a hydrolyzable group. The hydroxy group may be, but is not limited to, a group generated by hydrolysis of a hydrolyzable group.

$R^{d2}$ is preferably —OR, wherein R is a substituted or unsubstituted $C_{1-3}$ alkyl group, more preferably a methyl group.

In the formula, $R^{d3}$s are the same as or different from each other, and are each a hydrogen atom or a lower alkyl group. The lower alkyl group is preferably a C1-C20 alkyl group, more preferably a C1-C6 alkyl group, still more preferably a methyl group.

In the formula, ps are the same as or different from each other, and are each an integer of 0 to 3; qs are the same as or different from each other, and are each an integer of 0 to 3; and rs are the same as or different from each other, and are each an integer of 0 to 3. The sum of p', q', and r' is 3.

In a preferred embodiment, q' in the terminal $R^{d'}$ in $R^d$ (or $R^d$, if $R^{d'}$ is absent) is preferably 2 or greater, such as 2 or 3, more preferably 3.

In a preferred embodiment, $R^d$ may contain, at an end thereof, at least one —Si(—Z—SiR$^{d2}_q$R$^{d3}_{r'}$)$_2$ or —Si(—Z—SiR$^{d2}_q$R$^{d3}_{r'}$)$_3$, preferably —Si(—Z—SiR$^{d2}_q$R$^{d3}_{r'}$)$_3$. In the formula, the (—Z—SiR$^{d2}_q$R$^{d3}_{r'}$) unit is preferably (—Z—SiR$^{d2}_3$). In a more preferred embodiment, all the ends of $R^d$ are preferably —Si(—Z—SiR$^{d2}_q$R$^{d3}_{r'}$)$_3$, and may be more preferably —Si(—Z—SiR$^{d2}_3$)$_3$.

The silane-containing reactive crosslinkable group also preferably contains a C1-C5 allyl group, a C1-C5 glycidyl group, an acryl group, or a methacryl group. In other words, in the silane-containing reactive crosslinkable group, at least one selected from $R^a$, $R^b$, and $R^c$ is preferably a C1-C5 allyl group, a C1-C5 glycidyl group, an acryl group, or a methacryl group.

$L^2$ is a single bond or a divalent linking group that directly binds to the ring in the formula (1). $L^2$ is preferably a single bond, an alkylene group, or a divalent group containing at least one bond selected from the group consisting of ether bond and ester bond, more preferably a single bond, a C1-C10 alkylene group, or a C1-C10 divalent hydrocarbon group containing at least one bond selected from the group consisting of ether bond and ester bond.

Specific examples of $L^2$ include —C$_2$H$_4$—, —C$_3$H$_6$—, —CO—O—CH$_2$—CH(OH)—CH$_2$—, —CH$_2$—, and —C$_4$H$_8$—.

Examples of the silane-containing reactive crosslinkable group include -L$^2$-SiR$^5_3$, -L$^2$-Si(OR$^6$)$_3$, -L$^2$-Si(NR$^6_2$)$_3$, and -L$^2$-Si(OCOR$^6$)$_3$, wherein $L^2$ is defined in the same manner as mentioned above; $R^5$ is a halogen atom; and $R^6$s are each independently a C1-C4 alkyl group.

Examples of the silicone residue include the following:

[Chem. 5]

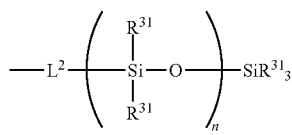

[Chem. 6]

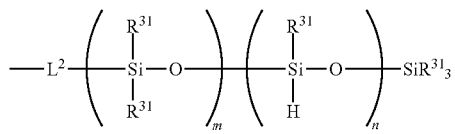

[Chem. 7]

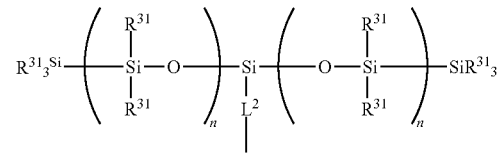

[Chem. 8]

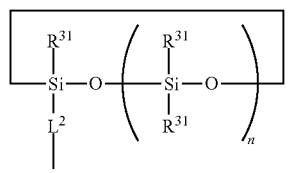

[Chem. 9]

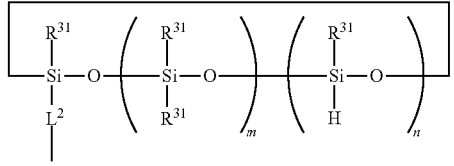

wherein $L^2$ is a single bond or a divalent linking group; n is an integer of 1 to 20; m is an integer of 0 to 10; $R^{31}$s are each independently a monovalent group; and at least one $R^{31}$ in each group is a reactive group.

$R^{31}$s in each group are each independently a monovalent group, and may be the reactive group or a group other than the reactive group. At least one $R^{31}$ in each group is the reactive group.

The reactive group is preferably at least one selected from the group consisting of H, a halogen atom, —OR$^{32}$ (wherein $R^{32}$ is a C1-C4 alkyl group or a C6-C20 aryl group), -L$^3$-SiR$^5_3$ (wherein $L^3$ is a single bond or a C1-C10 alkylene group; and $R^5$ is a halogen atom), -L$^3$-Si(OR$^6$)$_3$ (wherein $L^3$ is defined in the same manner as mentioned above; and $R^6$s are each independently a C1-C4 alkyl group), -L$^3$-Si(NR$^6_2$)$_3$ (wherein $L^3$ and $R^6$ are defined in the same manner as mentioned above), -L$^3$-Si(OCOR$^6$)$_3$ (wherein $L^3$ and $R^6$ are defined in the same manner as mentioned above), and a group containing any of these groups.

The group other than the reactive group is preferably at least one selected from the group consisting of an alkyl group, a halogenated alkyl group, an alkyl ester group, a halogenated alkyl ester group, an alkyl ether group, a halogenated alkyl ether group, an alkyl amide group, a halogenated alkyl amide group, a uril group, a halogenated uril group, a urea group, a halogenated urea group, —CONR$^k$COR$^l$ (wherein $R^k$ and $R^l$ are each independently H, an alkyl group, or a halogenated alkyl group), a glycan-containing group, an alkylene polyether group, an arene group, a halogenated arene group, a heterocycle-containing group, an aryl group, and a halogenated aryl group.

$L^2$ is a single bond or a divalent linking group that directly binds to the ring in the formula (1). Preferred examples of $L^2$ include those as mentioned above.

The silicone residue may also be any of the following:

[Chem. 10]

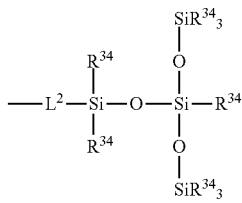

[Chem. 11]

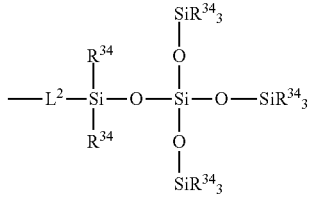

[Chem. 12]

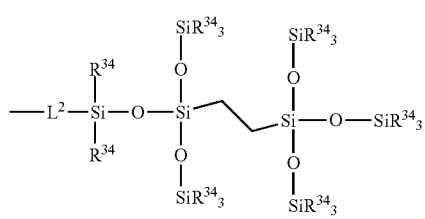

[Chem. 13]

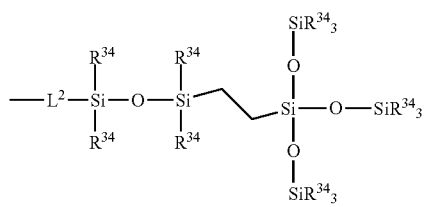

[Chem. 14]

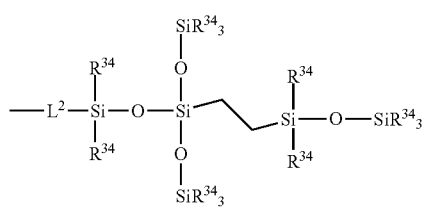

[Chem. 15]

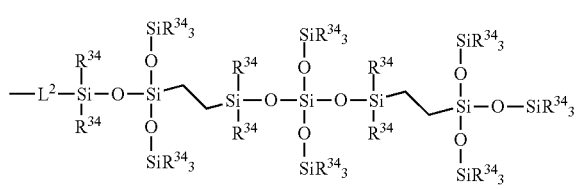

[Chem. 16]

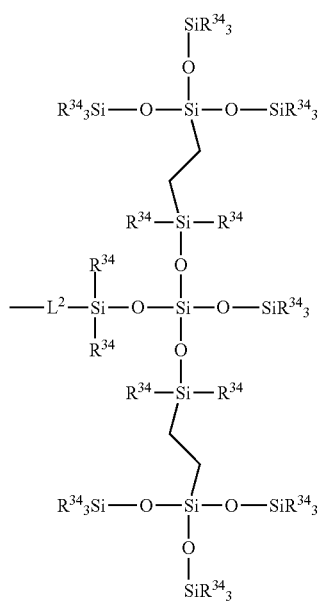

[Chem. 17]

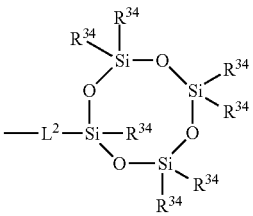

[Chem. 18]

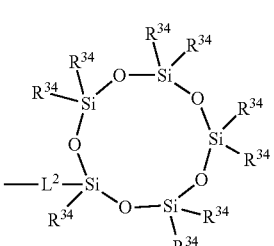

wherein $L^2$ is a single bond or a divalent linking group; $R^{34}$s are each independently a monovalent group; and at least one $R^{34}$ in each group is a reactive group.

$R^{34}$s in each group are each independently a monovalent group, and may be the reactive group or a group other than the reactive group. At least one $R^{34}$ in each group is the reactive group.

The reactive group is preferably at least one selected from the group consisting of —H, —OR$^{35}$ (wherein R$^{35}$ is a C1-C4 alkyl group), a halogen atom, —OH, —O—CR$^{35}$=CH$_2$ (wherein R$^{35}$ is defined in the same manner as mentioned above), —OCOR$^{35}$ (wherein R$^{35}$ is defined in the same manner as mentioned above), —OCO—OR$^j$ (wherein R$^j$ is an alkyl group or a halogenated alkyl group), —NR$^{35}{}_2$ (wherein R$^{35}$ is defined in the same manner as mentioned above), and a group containing any of these groups.

The group other than the reactive group is preferably at least one selected from the group consisting of an alkyl group, a halogenated alkyl group, an alkyl ester group, a halogenated alkyl ester group, an alkyl ether group, a halogenated alkyl ether group, an alkyl amide group, a halogenated alkyl amide group, a uril group, a halogenated uril group, a urea group, a halogenated urea group, —CONR$^k$COR$^l$ (wherein R$^k$ and R$^l$ are each independently H, an alkyl group, or a halogenated alkyl group), a glycan-containing group, an alkylene polyether group, an arene group, a halogenated arene group, a heterocycle-containing group, an aryl group, and a halogenated aryl group.

$L^2$ is a single bond or a divalent linking group that directly binds to the ring in the formula (1). Preferred examples of $L^2$ include those as mentioned above.

Examples of the silsesquioxane residue include the following:

[Chem. 19]

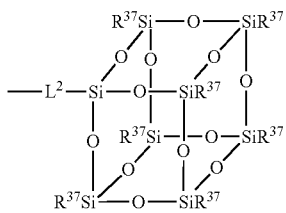

[Chem. 20]

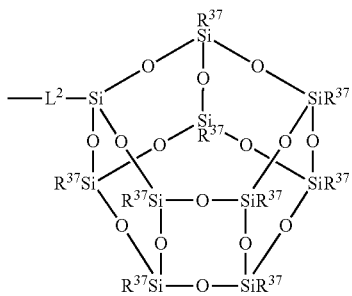

[Chem. 21]

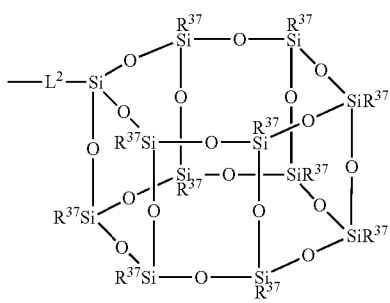

[Chem. 22]

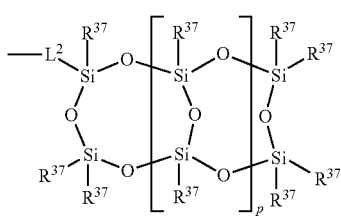

[Chem. 23]

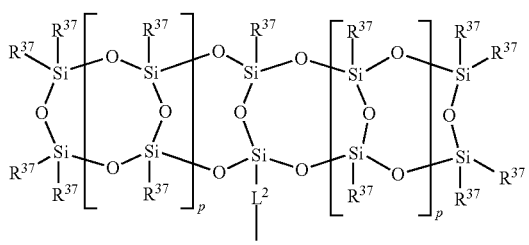

wherein $L^2$ is a single bond or a divalent linking group; $R^{37}$s are each independently a monovalent group; at least one $R^{37}$ in each group is a reactive group; and ps are each independently an integer of 0 to 5000.

$R^{37}$s in each group are each independently a monovalent group, and may be the reactive group or a group other than the reactive group. At least one $R^{37}$ in each group is the reactive group.

The reactive group is preferably at least one selected from the group consisting of —H, —OR$^{35}$ (wherein R$^{35}$ is a C1-C4 alkyl group), a halogen atom, —OH, —O—CR$^{35}$=CH$_2$ (wherein R$^{35}$ is defined in the same manner as mentioned above), —OCOR$^{35}$ (wherein R$^{35}$ is defined in the same manner as mentioned above), —OCO-OR$^j$ (wherein R$^j$ is an alkyl group or a halogenated alkyl group), —NR$^{35}{}_2$ (wherein R$^{35}$ is defined in the same manner as mentioned above), and a group containing any of these groups.

The group other than the reactive group is preferably at least one selected from the group consisting of an alkyl group, a halogenated alkyl group, an alkyl ester group, a halogenated alkyl ester group, an alkyl ether group, a halogenated alkyl ether group, an alkyl amide group, a halogenated alkyl amide group, a uril group, a halogenated uril group, a urea group, a halogenated urea group, —CONR$^k$COR$^l$ (wherein R$^k$ and R$^l$ are each independently H, an alkyl group, or a halogenated alkyl group), a glycan-containing group, an alkylene polyether group, an arene group, a halogenated arene group, a heterocycle-containing group, an aryl group, and a halogenated aryl group.

$L^2$ is a single bond or a divalent linking group that directly binds to the ring in the formula (1). Preferred examples of $L^2$ include those as mentioned above.

In the compound represented by the formula (1), $R^1$ has an average molecular weight of 500 to 30000, preferably 1500 to 30000, more preferably 2000 to 10000, although not limited thereto.

The compound represented by the formula (1) may have an average molecular weight of $5\times10^2$ to $1\times10^5$, although not limited thereto. In order to achieve good UV resistance and friction durability, the average molecular weight is preferably 2000 to 30000, more preferably 2500 to 12000. The term "average molecular weight" as used herein means the number average molecular weight, and the "average molecular weight" is a value determined by $^{19}$F-NMR.

The compound represented by the formula (1) is a novel compound, and may be produced by the following production method, for example.

The compound may be produced by reacting an isocyanuric acid derivative compound represented by the following formula:

[Chem. 24]

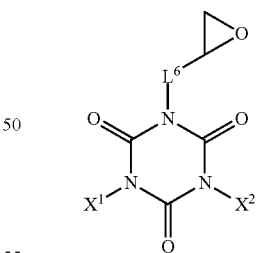

(wherein $X^1$ and $X^2$ are defined in the same manner as mentioned above; and $L^4$ is a single bond or a divalent linking group) and a compound represented by $R^{41}$—COOH (wherein $R^{41}$ is a monovalent organic group constituting the above $R^1$ together with —COO—CH$_2$CH(OH)-L$^4$-).

$R^{41}$ constitutes the above $R^1$ together with —COO—CH$_2$CH(OH)-L$^4$-, and thus naturally contains the polyether chain. This reaction generates a monovalent organic group represented by $R^{41}$—COO—CH$_2$CH(OH)-L$^4$-. $R^{41}$ is preferably a monovalent organic group represented by $R^3$—(OR$^2$)$_a$-L$^5$-, wherein (OR$^2$)$_a$ is the polyether chain; $R^3$ is an alkyl group or a fluorinated alkyl group; and $L^5$ is a single bond or a divalent linking group constituting the above L together with —COO—CH$_2$CH(OH)-L$^4$-.

The compound may also be produced by reacting an isocyanuric acid derivative compound represented by the following formula:

[Chem. 25]

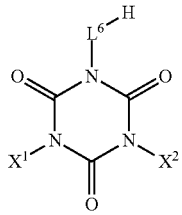

(wherein $X^1$ and $X^2$ are defined in the same manner as mentioned above; and $L^6$ is a single bond or a divalent linking group) and a compound represented by $R^{42}$—O—SO$_2R^{43}$ (wherein $R^{42}$ is a monovalent organic group constituting the above $R^1$ together with -L$^6$-; and $R^{43}$ is an alkyl group or a fluorinated alkyl group) or $R^{42}$—$X^{26}$ (wherein $R^{42}$ is defined in the same manner as mentioned above; and $X^{26}$ is Cl, Br, or I).

$R^{42}$ constitutes the above $R^1$ together with -L$^6$-, and thus naturally contains the polyether chain. This reaction generates a monovalent organic group represented by $R^{42}$-L$^6$-. $R^{42}$ is more preferably a monovalent organic group represented by $R^3$—(OR$^2$)$_a$-L$^7$-, wherein (OR$^2$)$_a$ is the polyether chain; $R^3$ is an alkyl group or a fluorinated alkyl group; and $L^7$ is a single bond or a divalent linking group constituting the above L together with -L$^6$-.

Also, in any of the above production methods, for example, at least one selected from the group consisting of the silane-containing reactive crosslinkable group, -L$^2$-SiR$^5$$_3$, -L$^2$-Si(OR$^6$)$_3$, -L$^2$-Si(NR$^6$$_2$)$_3$, and -L$^2$-Si(OCOR$^6$)$_3$ (wherein $L^2$ is a single bond or a divalent linking group; $R^5$ is a halogen atom; and $R^6$s are each independently a C1-C4 alkyl group) can be introduced as $X^1$ and/or $X^2$ by introducing a double-bond-containing group (preferably, an allyl group) as a group corresponding to $X^1$ and/or $X^2$, and then reacting the above group with a double bond and a compound represented by H—{Si(R$^a$)$_s$(R$^b$)$_t$(R$^c$)$_u$(R$^d$)$_v$}$_n$ (wherein R$^a$, R$^b$, R$^c$, R$^d$, s, t, u, v, and n are defined in the same manner as mentioned above) to introduce the structure represented by -L$^2$-{Si(R$^a$)$_s$(R$^b$)$_t$(R$^c$)$_u$(R$^d$)$_v$}$_n$ (wherein L$^2$, R$^a$, R$^b$, R$^c$, R$^d$, s, t, u, v, and n are defined in the same manner as mentioned above) into the compound.

The surface-treating layer may be either a monolayered one or a multilayered one.

The substrates of the invention each may be an optical material.

Preferred examples of the optical material include optical materials relating to displays to be mentioned below, as well as a wide variety of optical materials, such as displays, including cathode ray tubes (CRTs, e.g., TVs and monitors for personal computers), liquid crystal displays, plasma displays, organic EL displays, inorganic thin-film EL dot matrix displays, rear projection displays, vacuum fluorescent displays (VFDs), and field emission displays (FEDs); protective plates therefor, and those prepared by subjecting a surface thereof to an antireflection film treatment.

The substrates of the invention each may be, but not limited to, an optical member. Examples of the optical member include: lenses of eyeglasses; front surface protective plates, antireflection plates, polarizing plates, and antiglare plates for displays such as PDPs and LCDs; touch-screen sheets for devices such as mobile phones and personal digital assistants; disc surfaces of optical discs such as Blu-ray® discs, DVDs, CD-Rs, and MO discs; and optical fibers.

The substrates of the invention each may be medical equipment or a medical material.

The surface-treating layer may have any thickness. For the substrates of the invention which are optical members, the thickness of the surface-treating layer is preferably 1 to 50 nm, more preferably 1 to 30 nm, particularly preferably 1 to 15 nm, so as to achieve good UV resistance, optical performance, surface lubricity, friction durability, and antifouling property.

In general, windowpanes for vehicles and windowpanes for buildings are desired to be free from attachment of obstructions to the visibility, such as water drops or soil, on the surfaces thereof. For example, obstructions such as raindrops, dust, or soil attached to the surface of a windowpane for a vehicle, or the moisture condensed thereon due to the influence of atmospheric humidity and temperature, may impair the transparency and the see-through visibility of the windowpane, hindering the driving and controlling of the vehicle such as an automobile. Thus, water drops attached to windowpanes for automobiles are removed by a physical way, such as wiping with wipers or wiping by hand. Accordingly, these windowpanes for vehicles and windowpanes for buildings need to exhibit excellent water-repellency and antifouling property, as well as weather resistance and abrasion resistance which allow the former properties to last for a long period of time. The substrates of the invention each can suitably be used for the above windowpanes for vehicles and windowpanes for buildings.

In order to achieve excellent transparency when applied to a windowpane for a vehicle or a windowpane for a building, the substrates of the invention each preferably have an average transmittance within the visible light range of 85% or higher, preferably 90% or higher, and a haze of 8.0% or lower.

The average transmittance within the visible light range as used in the invention is defined as the average value of the transmittances determined at every 5-nm or wider range within the visible light range from 400 to 700 nm. The transmittances of the respective measurement wavelengths can be determined using a conventionally known measurement device, such as a spectrophotometer UVIDFC-610 (Shimadzu Corp.), or a self-registering spectrophotometer model 330, a self-registering spectrophotometer model U-3210, a self-registering spectrophotometer model U-3410, or a self-registering spectrophotometer model U-4000 (Hitachi, Ltd.).

The substrates of the invention each can also suitably be used for interior or exterior windows for buildings, glasses and lenses of eyeglasses, windshields, side windows, rear windows, quarter windows, and side view mirrors of vehicles, watches and swimming goggles, glass covers of devices and apparatuses, motorcycle helmets and windshields for helmets, glass lenses such as telescope lenses and camera lenses, glass safety screens, transparent separation equipment such as spray protective walls, glass doors or windows or plastic windows for devices or apparatuses such as chemical reaction hoods, biological or medical hoods, culture vessels, cabinets, microwave ovens, toaster ovens, and refrigerators, display windows, security glasses, taps for waterworks made of stainless steel, and showerheads.

The term "vehicle" as used herein means any of vehicles such as passenger cars, vans, minivans, buses, sport utility vehicles (SUVs), trucks, semi-trailers, trains, trams, tractors, motorcycles, trailers, small trucks, large vehicle earthmovers such as bulldozers, crane trucks and earthmovers, airplanes, boats, ships, rockets, and other types of transports.

A windshield can be fixed on a vehicle, and is removable or detachable from the vehicle. A windshield can typically be made of reinforced glass, a polymer material such as plastic, or a polymer-reinforced or laminated glass. A typical windshield of an automobile may include two or more glass sheets with a plastic layer interposed therebetween. Other windows of a vehicle such as a side window, a rear window, and a quarter window may also be any of the substrates of the invention. In order to provide good see-through visibility, the windshield of a vehicle needs to be water repellent. Thus, no raindrops, spray of water, or dust attach to the windshield.

For the substrates of the invention which are onboard glasses, building materials, or stones as described for the substrate, the surface-treating layer preferably has a thickness of 1 nm to 20 μm, more preferably 3 nm to 1 μm, particularly preferably 5 to 100 nm, so as to achieve good UV resistance, surface lubricity, friction durability, and antifouling property.

The substrates of the invention which are windshields, the substrates each may have a thickness of 2 to 30 mm. In order to maintain the strength of the glass, the thickness may be 3 mm or greater and 20 mm or smaller, more preferably 4 mm or greater and 8 mm or smaller. The substrates of the invention which are side windows or rear windows each may have a thickness of 3 to 15 mm, preferably 4 to 7 mm.

The substrates each may include an intermediate layer between the surface-treating layer and the substrate, or the surface-treating layer may be disposed directly on the substrate. In order to sufficiently exert the properties of the substrate itself, to produce the substrate easily, and to lead to economic advantages, the surface-treating layer is preferably disposed directly on the substrate.

The surface-treating layer may further contain any of additives such as antioxidants, thickening agents, leveling agents, antifoams, antistatic agents, antifogging agents, ultraviolet absorbers, pigments, dyes, inorganic fine particles such as silica, fillers such as aluminum paste, talc, glass frit, and metal powder, and polymerization inhibitors such as butylated hydroxytoluene (BHT) and phenothiazine (PTZ).

The surface-treating layer may be formed by applying the compound represented by the formula (1) to a surface of the substrate so as to coat the surface. The surface-treating layer may be formed by any method. For example, a wet coating method or a dry coating method may be used.

Examples of the wet coating method include immersion coating, spin coating, flow coating, spray coating, roll coating, gravure coating, and other similar methods.

Examples of the dry coating method include deposition (usually, vacuum deposition), sputtering, CVD, and other similar methods. Specific examples of the deposition method (usually, vacuum deposition method) include resistance heating, high-frequency heating utilizing electron beams or microwaves, ion beams, and other similar methods. Specific examples of the CVD method include plasma CVD, optical CVD, thermal CVD, and other similar methods.

The coating may also be achieved by an atmospheric pressure plasma method.

The compound represented by the formula (1) may be impregnated into a porous material such as a porous ceramic material or flocs of metal fiber such as steel wool to provide pellets. These pellets can be used in vacuum deposition, for example.

In the case of a wet coating method, the surface-treating layer may be formed by applying a composition containing the compound represented by the formula (1) and a solvent to the substrate.

Examples of the solvent include a fluorine-containing organic solvent and a fluorine-free organic solvent.

Examples of the fluorine-containing organic solvent include perfluorohexane, perfluorooctane, perfluoromethylcyclohexane, perfluorodimethylcyclohexane, perfluorodecalin, perfluoroalkyl ethanol, perfluorobenzene, perfluorotoluene, perfluoroalkyl amine (e.g., Florinert (trade name)), perfluoroalkyl ether, perfluorobutyltetrahydrofuran, polyfluoroaliphatic hydrocarbon (Asahiklin AC6000 (trade name)), hydrochlorofluorocarbon (e.g., Asahiklin AK-225 (trade name)), hydrofluoroether (e.g., Novec (trade name), HFE-7100 (trade name), HFE-7200 (trade name), HFE-7300 (trade name)), HFE-7000 (trade name), Asahiklin AE-3000 (trade name)), 1,1,2,2,3,3,4-heptafluorocyclopentane, 1,1,1,3,3-pentafluorobutane, fluorine-containing alcohol, perfluoroalkyl bromide, perfluoroalkyl iodide, perfluoropolyether (e.g., Krytox (trade name), Demnum (trade name), Fomblin (trade name)), 1,3-bistrifluoromethylbenzene, 2-(perfluoroalkyl)ethyl methacrylate, 2-(perfluoroalkyl)ethyl acrylate, perfluoroalkylethylene, Freon 134a, hexafluoropropene oligomers, and 1,2-dichloro-1,3,3,3-tetrafluoro-1-propene.

Examples of the fluorine-free organic solvent include acetone, methyl isobutyl ketone, cyclohexanone, propylene glycol monomethyl ether, propylene glycol monoethyl ether, propylene glycol monobutyl ether, propylene glycol monomethyl ether acetate, propylene glycol monoethyl ether acetate, propylene glycol monobutyl ether acetate, dipropylene glycol dimethyl ether pentane, hexane, heptane, octane, hexadecane, dichloromethane, chloroform, carbon tetrachloride, dichloroethane, carbon disulfide, benzene, toluene, xylene, nitrobenzene, diethyl ether, dimethoxyethane, diglyme, triglyme, ethyl acetate, butyl acetate, dimethyl formamide, dimethyl sulfoxide, 2-butanone, acetonitrile, benzonitrile, butanol, 1-propanol, 2-propanol, ethanol, methanol, and diacetone alcohol.

The solvent is preferably methyl isobutyl ketone, propylene glycol monomethyl ether, hexadecane, butyl acetate, acetone, 2-butanone, cyclohexanone, ethyl acetate, diacetone alcohol, or 2-propanol.

These solvents may be used alone or in combination of two or more. The fluorine-free organic solvent, if used, is preferably used in combination with the fluorine-containing organic solvent.

The solvent is preferably used in an amount of 1 to 99.99% by mass in the composition. This amount is more preferably 10 to 99.9% by mass, still more preferably 50 to 99% by mass.

The composition may further contain, in addition to the compound represented by the formula (1) and a solvent, any of additives such as antioxidants, thickening agents, leveling agents, antifoams, antistatic agents, antifogging agents, ultraviolet absorbers, pigments, dyes, inorganic fine particles such as silica, fillers such as aluminum paste, talc, glass frit, and metal powder, polymerization inhibitors such as butylated hydroxytoluene (BHT) and phenothiazine (PTZ), catalysts, and other additional components.

Examples of the catalysts include acids (e.g., acetic acid, trifluoroacetic acid), bases (e.g., ammonia, triethylamine, diethylamine), and transition metals (e.g., Ti, Ni, Sn).

The catalyst(s) may be present in an amount of 1 ppm by mass to 5% by mass, preferably 5 to 5000 ppm by mass, more preferably 10 to 1000 ppm by mass, relative to the compound represented by the formula (1).

The catalysts promote hydrolysis and dehydration condensation of the compound represented by the formula (1), and promote formation of the surface-treating layer.

In addition to the above, examples of the additional components include tetraethoxysilane, methyltrimethoxysilane, 3-aminopropyltrimethoxysilane, 3-glycidoxypropyltrimethoxysilane, and methyltriacetoxysilane. The amount thereof is 10 ppm by mass to 20% by mass, preferably 3 ppm by mass to 5% by mass, more preferably 10 ppm by mass to 1% by mass, relative to the compound represented by the formula (1). Examples of the additional components further include different surface-treating compounds, (non-reactive) fluoropolyether compounds, preferably perfluoro(poly)ether compounds each of which can be regarded as a fluorine-containing oil (hereinafter, they are referred to as "fluorine-containing oils"), and (non-reactive) silicone compounds each of which can be regarded as a silicone oil (hereinafter, they are referred to as "silicone oils").

The different surface-treating compounds each may be, but are not limited to, at least one perfluoro(poly)ether group-containing silane compound represented by any of the following formulae (1A), (2A), (1B), (2B), (1C), (2C), (1D), and (2D):

[Chem. 26]

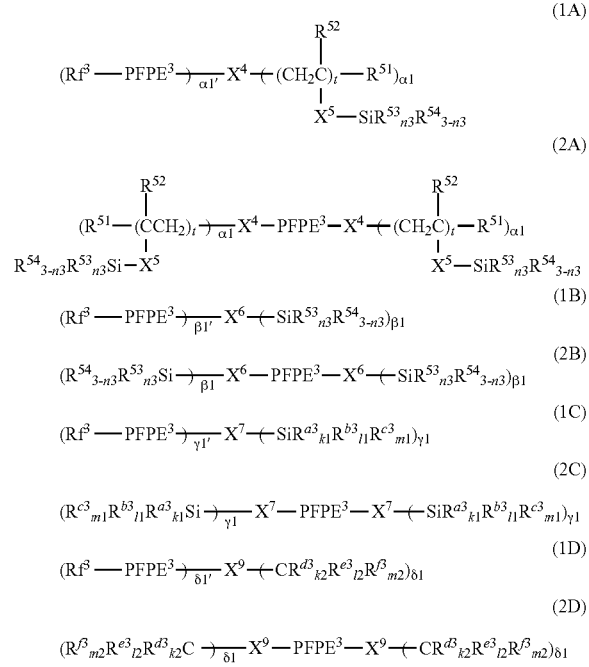

wherein
PFPE$^3$s are the same as or different from each other, and are each a group represented by the following formula:

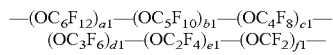

(wherein a1, b1, c1, d1, e1, and f1 are each independently an integer of 0 or greater and 200 or smaller; the sum of a1, b1, c1, d1, e1, and f1 is at least 1; and the repeating units parenthesized with a1, b1, c1, d1, e1, or f1 are present in any order in the formula), Rf$^3$s are the same as or different from each other, and are each a C1-C16 alkyl group optionally substituted with one or more fluorine atoms;

R$^{53}$s are the same as or different from each other, and are each a hydroxy group or a hydrolyzable group;

R$^{54}$s are the same as or different from each other, and are each a hydrogen atom or a C1-C22 alkyl group;

R$^{51}$s are the same as or different from each other, and are each a hydrogen atom or a halogen atom;

R$^{52}$s are the same as or different from each other, and are each a hydrogen atom or a lower alkyl group;

n3s are each an integer of 0 to 3 independently for each ($-$SiR$^{51}_{n3}$R$^{52}_{3-n3}$) unit;

at least one n3 is an integer of 1 to 3 in the formulae (1A), (2A), (1B), and (2B);

X$^4$s are each independently a single bond or a divalent to decavalent organic group;

X$^5$s are the same as or different from each other, and are each a single bond or a divalent organic group;

ts are the same as or different from each other, and are each an integer of 1 to 10;

α1s are each independently an integer of 1 to 9;

α1's are each independently an integer of 1 to 9;

X$^6$s are each independently a single bond or a divalent to decavalent organic group;

β1s are each independently an integer of 1 to 9;

β1's are each independently an integer of 1 to 9;

X$^7$s are each independently a single bond or a divalent to decavalent organic group;

γ1s are each independently an integer of 1 to 9;

γ1's are each independently an integer of 1 to 9;

R$^{a3}$s are the same as or different from each other, and are each $-$Z$^3$$-$SiR$^{61}_{p1}$R$^{62}_{q1}$R$^{63}_{r1}$;

Z$^3$s are the same as or different from each other, and are each an oxygen atom or a divalent organic group;

R$^{61}$s are the same as or different from each other, and are each R$^{a3}$';

R$^{a3}$' is defined in the same manner as R$^{a3}$;

in R$^{a3}$, the number of Si atoms linearly linked via a Z$^3$ group is at most five;

R$^{62}$s are the same as or different from each other, and are each a hydroxy group or a hydrolyzable group;

R$^{63}$s are the same as or different from each other, and are each a hydrogen atom or a lower alkyl group;

p1s are the same as or different from each other, and are each an integer of 0 to 3;

q1s are the same as or different from each other, and are each an integer of 0 to 3;

r1s are the same as or different from each other, and are each an integer of 0 to 3;

at least one q1 is an integer of 1 to 3 in the formulae (1C) and (2C);

R$^{b3}$s are the same as or different from each other, and are each a hydroxy group or a hydrolyzable group;

R$^{c3}$s are the same as or different from each other, and are each a hydrogen atom or a lower alkyl group;

k1s are the same as or different from each other, and are each an integer of 1 to 3;

l1s are the same as or different from each other, and are each an integer of 0 to 2;

m1s are the same as or different from each other, and are each an integer of 0 to 2;

$X^9$s are each independently a single bond or a divalent to decavalent organic group;

δ1s are each independently an integer of 1 to 9;

δ1's are each independently an integer of 1 to 9;

$R^{d3}$s are the same as or different from each other, and are each $—Z^4—CR^{71}_{p2}R^{72}_{q2}R^{73}_{r2}$;

$Z^4$s are the same as or different from each other, and are each an oxygen atom or a divalent organic group;

$R^{71}$s are the same as or different from each other, and are each $R^{d3'}$;

$R^{d3'}$ is defined in the same manner as $R^{d3}$;

in $R^{d3}$, the number of C atoms linearly linked via a $Z^4$ group is at most five;

$R^{72}$s are the same as or different from each other, and are each $—Y—SiR^{74}_{n2}R^{75}_{3-n2}$;

Ys are the same as or different from each other, and are each a divalent organic group;

$R^{74}$s are the same as or different from each other, and are each a hydroxy group or a hydrolyzable group;

$R^{75}$s are the same as or different from each other, and are each a hydrogen atom or a lower alkyl group;

n2s are each an integer of 1 to 3 independently for each ($—Y—SiR^{74}_{n2}R^{75}_{3-n2}$) unit;

at least one n2 is an integer of 1 to 3 in the formulae (1D) and (2D);

$R^{73}$s are the same as or different from each other, and are each a hydrogen atom or a lower alkyl group;

p2s are the same as or different from each other, and are each an integer of 0 to 3;

q2s are the same as or different from each other, and are each an integer of 0 to 3;

r2s are the same as or different from each other, and are each an integer of 0 to 3;

$R^{e3}$s are the same as or different from each other, and are each $—Y—SiR^{74}_{n2}R^{75}_{3-n2}$;

$R^{f3}$s are the same as or different from each other, and are each a hydrogen atom or a lower alkyl group;

k2s are the same as or different from each other, and are each an integer of 0 to 3;

l2s are the same as or different from each other, and are each an integer of 0 to 3;

m2s are the same as or different from each other, and are each an integer of 0 to 3; and at least one q2 is 2 or 3 or at least one l2 is 2 or 3 in the formulae (1D) and (2D).

Examples of the fluorine-containing oils include, but not limited to, compounds (perfluoro(poly)ether compounds) represented by the following formula (3):

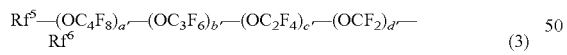

(3)

wherein $Rf^5$ is a C1-C16 alkyl group (preferably, a $C_{1-16}$ perfluoroalkyl group) optionally substituted with one or more fluorine atoms; $Rf^6$ is a C1-C16 alkyl group (preferably, a $C_{1-16}$ perfluoroalkyl group) optionally substituted with one or more fluorine atoms, a fluorine atom, or a hydrogen atom; $Rf^5$ and $Rf^6$ are more preferably each independently a $C_{1-3}$ perfluoroalkyl group.

In the formula, a', b', c', and d' are the numbers of four repeating units of the perfluoro(poly)ether constituting the main backbone of the polymer, and are each independently an integer of 0 or greater and 300 or smaller. The sum of a', b', c', and d' is at least 1, preferably 1 to 300, more preferably 20 to 300. The repeating units parenthesized with the subscript a', b', c', or d' are present in any order in the formula. For these repeating units, $—(OC_4F_8)—$ may be any of $—(OCF_2CF_2CF_2CF_2)—$, $—(OCF(CF_3)CF_2CF_2)—$, $—(OCF_2CF(CF_3)CF_2)—$, $—(OCF_2CF_2CF(CF_3))—$, $—(OC(CF_3)_2CF_2)—$, $—(OCF_2C(CF_3)_2)—$, $—(OCF(CF_3)CF(CF_3))—$, $—(OCF(C_2F_5)CF_2)—$, and $—(OCF_2CF(C_2F_5))—$, and is preferably $—(OCF_2CF_2CF_2CF_2)—$; $—(OC_3F_6)—$ may be any of $—(OCF_2CF_2CF_2)—$, $—(OCF(CF_3)CF_2)—$, and $—(OCF_2CF(CF_3))—$, and is preferably $—(OCF_2CF_2CF_2)—$; and $—(OC_2F_4)—$ may be any of $—(OCF_2CF_2)—$ and $—(OCF(CF_3))—$, and is preferably $—(OCF_2CF_2)—$.

The perfluoro(poly)ether compound represented by the formula (3) may be a compound (optionally, a mixture of one or two or more thereof) represented by any of the following formulae (3a) and (3b):

(3a)

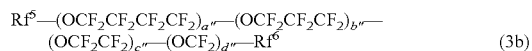

(3b)

wherein $Rf^5$ and $Rf^6$ are defined in the same manner as mentioned above; in the formula (3a), b" is an integer of 1 or greater and 100 or smaller; in the formula (3b), a" and b" are each independently an integer of 1 or greater and 30 or smaller, and c" and d" are each independently an integer of 1 or greater and 300 or smaller; and the repeating units parenthesized with the subscript a", b", c", or d" are present in any order in the formula.

The fluorine-containing oil may have an average molecular weight of 1000 to 30000. This can lead to high surface lubricity.

The composition may contain a fluorine-containing oil in an amount of 0 to 400 parts by mass, for example, preferably 0 to 200 parts by mass, more preferably 0. 1 to 50 parts by mass, relative to 100 parts by mass of the sum of the composition (when each component includes two or more types thereof, the sum of them; the same applies to the following).

The fluorine-containing oil contributes to improvement of the surface lubricity of the surface-treating layer while maintaining the UV resistance.

The composition may further contain a compound represented by the following formula (2):

[Chem. 27]

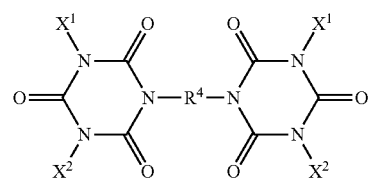

wherein $X^1$ and $X^2$ are defined in the same manner as mentioned above; and $R^4$ is a divalent organic group containing a polyether chain, the polyether chain being at least one chain selected from the group consisting of:

a chain represented by the following formula:

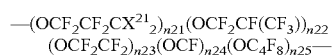

wherein n21, n22, n23, n24, and n25 are each independently an integer of 0 or 1 or greater; $X^{21}$s are each independently H, F, or Cl; and the repeating units are present in any order; and a chain represented by the following formula:

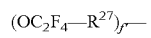

wherein $R^{27}$ is a group selected from $OC_2F_4$, $OC_3F_6$, and $OC_4F_8$; and f' is an integer of 2 to 100.

The composition may contain a compound represented by the formula (2) in an amount of 0 to 100 parts by mass, for example, preferably 0 to 50 parts by mass, more preferably 0 to 25 parts by mass, relative to 100 parts by mass of the sum of the above components (when each component includes two or more types thereof, the sum of them; the same applies to the following).

In the case of a dry coating method, the surface-treating layer may be formed by subjecting a compound represented by the formula (1) directly to a dry coating method, or may be formed by subjecting the composition to a dry coating method.

The surface-treating layer is preferably formed such that the compound represented by the formula (1) coexists with a catalyst for hydrolysis and dehydration condensation in the surface-treating layer. Briefly, in the case of a wet coating method, the process may be such that the compound represented by the formula (1) is diluted in a solvent, and a catalyst is added to the dilution of the compound represented by the formula (1) immediately before the dilution is applied to the substrate surface. In the case of a dry coating method, the process may be such that the surface treating agent in the invention mixed with a catalyst is directly used for deposition (usually, vacuum deposition), or that the compound represented by the formula (1) mixed with a catalyst is impregnated into a porous medium of metal such as iron or copper to prepare a pelletized substance, and this pelletized substance is used for deposition (usually, vacuum deposition).

Next, if necessary, the surface-treating layer is subjected to post-treatment. This post-treatment may be, but is not limited to, water supply and dry heating in succession, and may specifically be performed as follows.

After the surface-treating layer is formed on the substrate surface as mentioned above, this surface-treating layer (hereinafter, also referred to as a "precursor layer") is supplied with water. Water may be supplied by a method such as, but not limited to, dew condensation owing to a difference in temperature between the precursor layer (and the substrate) and the ambient atmosphere or spraying of vapor (steam).

Water supply may be performed in an atmosphere at a temperature of, for example, 0° C. to 250° C., preferably 60° C. or higher, more preferably 100° C. or higher, while preferably 180° C. or lower, more preferably 150° C. or lower. Water supply at a temperature within such a range allows hydrolysis to proceed. The pressure at this time may conveniently be, but not limited to, an atmospheric pressure.

Then, the precursor layer is heated on the substrate surface in a dry atmosphere at a temperature exceeding 60° C. The dry heating may be performed by, but not limited to, leaving the precursor layer together with the substrate in an atmosphere at a temperature exceeding 60° C., preferably exceeding 100° C., while 250° C. or lower, preferably 180° C. or lower, and at an unsaturated vapor pressure. The pressure at this time may conveniently be, but not limited to, an atmospheric pressure.

In such an atmosphere, groups binding to Si atoms after hydrolysis are rapidly dehydration-condensed between molecules of the compound represented by the formula (1). Further, groups binding to Si atoms after hydrolysis of the compound and reactive groups present on the substrate surface rapidly react with each other between the compound and the substrate. When the reactive groups present on the substrate surface are hydroxy groups, they are dehydration-condensed. As a result, the compound represented by the formula (1) and the substrate form a bond.

The above water supply and dry heating may continually be performed using superheated vapor.

Thereby, the post-treatment may be performed. The post-treatment may be performed so as to maintain high UV resistance and to further improve the friction durability. Still, it should be noted that the post-treatment is not essential for production of the substrates of the invention. For example, the surface-treating layer formed on the substrate surface may only be left as it is.

Thereby, the surface-treating layer is formed on the substrate surface and any of the substrates of the invention is produced. The surface-treating layer thereby obtained exhibits good UV resistance. In addition to good UV resistance, this surface-treating layer may also exhibit properties such as water-repellency, oil-repellency, antifouling property (e.g., an ability to prevent sticking of dirt such as fingerprints), surface lubricity (or lubrication, e.g., ease of wiping of dirt such as fingerprints, excellent texture when touched with a finger), and high friction durability, in accordance with the components of the composition used, and may suitably be used as a functional film.

EXAMPLES

The invention is described with reference to, but is not limited to, examples. In the following examples, all the formulae show the respective average compositions, and the repeating units (e.g., $CF_2CF_2CF_2O$, $CF_2CF_2O$, $CF_2O$) constituting the perfluoropolyether may be present in any order.

Synthesis Example 1: Method of Producing Perfluoropolyether (PFPE)-Containing Compound (A)

First, 2.0 g of 1,3-diallyl isocyanurate was dissolved in a solvent mixture of m-hexafluoroxylene and dimethyl formamide. Then, 1.0 g of potassium carbonate was added thereto and the components were heated under stirring. Further, 4.0 g of $CF_3CF_2CF_2O-(CF_2CF_2CF_2O)_{23}-CF_2CF_2CH_2$-trifluoromethane sulfonate dissolved in m-hexafluoroxylene was added thereto and the heating under stirring was continued. The completion of the reaction was confirmed by $^{19}F$-NMR and $^1H$-NMR. Pure water was added to the reaction solution and the resulting liquid was separated, whereby the following PFPE-containing compound (A) was obtained.

PFPE-Containing Compound (A):

[Chem. 28]

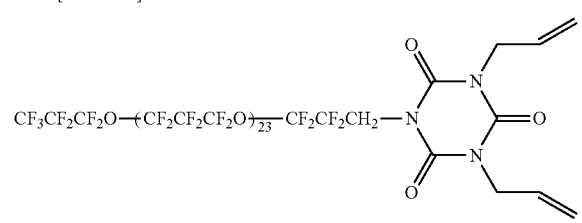

Synthesis Example 2: Method of Producing Perfluoropolyether (PFPE)-Containing Compound (B)

First, 10.1 g of the PFPE-containing compound (A), 40 g of m-hexafluoroxylene, 0.04 g of triacetoxymethylsilane, and 1.93 g of trichlorosilane were stirred at 10° C. for 30 minutes. Then, 0.115 ml of a xylene solution containing 2% Pt complex of 1,3-divinyl-1,1,3,3-tetramethyldisiloxane was added thereto and the components were heated and stirred for four hours. The volatile component was evaporated under reduced pressure. A solution mixture of 0.23 g of methanol and 6.1 g of trimethyl orthoformate was added and the components were heated and stirred for three hours. The resulting product was purified, whereby 9.9 g of the following PFPE-containing compound (B) containing trimethoxysilyl groups at ends was obtained.
PFPE-Containing Compound (B):

[Chem. 29]

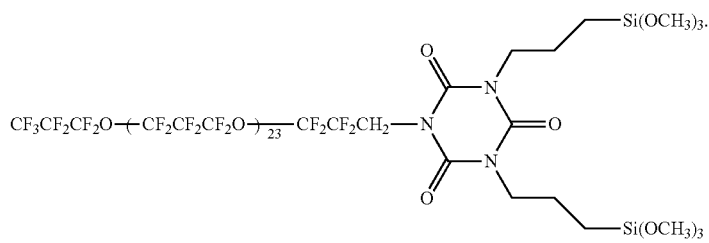

PFPE-Containing Compound (D):

[Chem. 31]

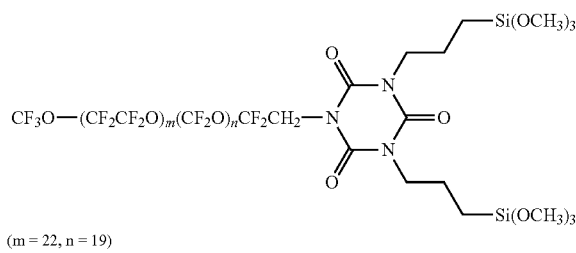

(m = 22, n = 19)

Synthesis Example 3: Method of Producing Perfluoropolyether (PFPE)-Containing Compounds (C) and (D)

First, 2.0 g of 1,3-diallyl isocyanurate was dissolved in a solvent mixture of m-hexafluoroxylene and dimethyl formamide. Then, 1.0 g of potassium carbonate was added thereto and the components were heated under stirring. Further, 4.0 g of CF$_3$O—(CF$_2$CF$_2$O)$_m$(CF$_2$O)$_n$CF$_2$CF$_2$CH$_2$-trifluoromethane sulfonate (m=22, n=19) dissolved in m-hexafluoroxylene was added thereto and the heating under stirring was continued. The completion of the reaction was confirmed by $^{19}$F-NMR and $^1$H-NMR. Pure water was added to the reaction solution and the resulting liquid was separated, whereby the following PFPE-containing compound (C) was obtained.
PFPE-Containing Compound (C):

[Chem. 30]

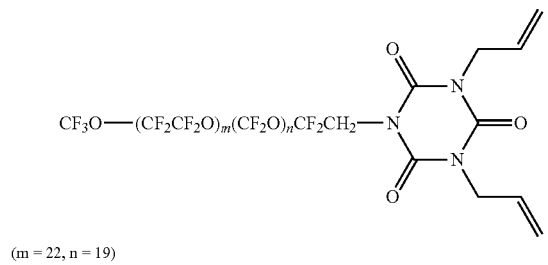

(m = 22, n = 19)

Then, 9.8 g of the following PFPE-containing compound (D) containing trimethoxysilyl groups at ends was obtained in the same manner as in Synthesis Example 2, except that the PFPE-containing compound (A) in Synthesis Example 2 was changed to the PFPE-containing compound (C).

Synthesis Example 4: Method of Producing Perfluoropolyether (PFPE)-Containing Compounds (I) and (J)

First, 10.0 g of the PFPE-containing compound (C), 45 g of m-hexafluoroxylene, 0.04 g of triacetoxymethylsilane, and 1.41 g of dichloromethylsilane were stirred at 10° C. for 30 minutes. Then, 0.136 ml of a xylene solution containing 2% Pt complex of 1,3-divinyl-1,1,3,3-tetramethyldisiloxane was added thereto and the components were heated and stirred. The volatile component was evaporated. Then, 15 ml of vinyl magnesium chloride (1.6 M THF solution) was added and the components were stirred at room temperature. The resulting product was purified, whereby 9.5 g of the following PFPE-containing compound (I) containing methyl divinyl silyl groups at ends was obtained.
PFPE-Containing Compound (I):

[Chem. 32]

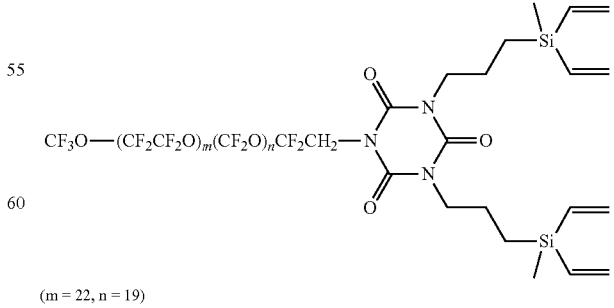

(m = 22, n = 19)

Next, 9.5 g of the PFPE-containing compound (I), 42 g of m-hexafluoroxylene, 0.04 g of triacetoxymethylsilane, and 2.30 g of trichlorosilane were stirred at 10° C. for 30 minutes. Then, 0.230 ml of a xylene solution containing 2% Pt complex of 1,3-divinyl-1,1,3,3-tetramethyldisiloxane was added thereto and the components were heated and stirred for four hours. The volatile component was evaporated. Then, a solution mixture of 0.30 g of methanol and 7.56 g of trimethyl orthoformate was added and the components were heated and stirred. The resulting product was purified, whereby 9.6 g of the following PFPE-containing compound (J) containing trimethoxysilyl groups at ends was obtained. PFPE-Containing Compound (J):

[Chem. 33]

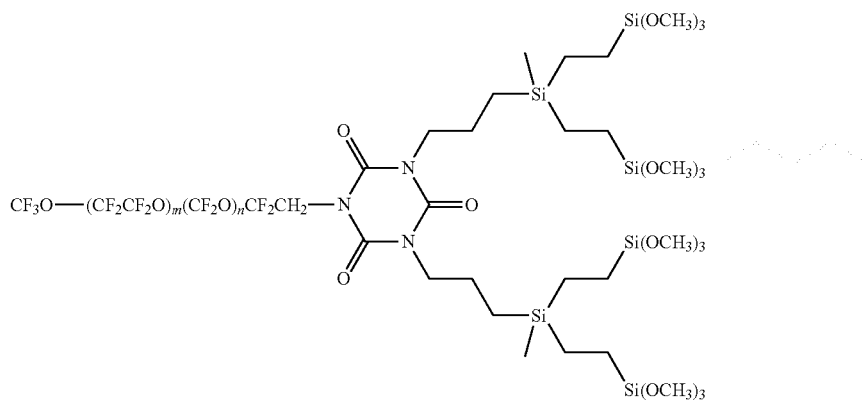

(m = 22, n = 19)

Example 1

The PFPE-containing compound (B) obtained in Synthesis Example 2 was dissolved in hydrofluoroether (Novec HFE7200, 3M Co.) so as to have a concentration of 20% by weight. Thereby, a surface-treating agent 1 was prepared.

The surface-treating agent 1 was vacuum-deposited on chemically strengthened glass ("Gorilla" Glass, Corning Inc., thickness: 0.7 mm). The vacuum deposition was performed under the following conditions. First, the pressure was adjusted to $3.0 \times 10^{-3}$ Pa and silicon dioxide was deposited on the surface of this chemically strengthened glass so as to have a thickness of 7 nm, whereby a silicon dioxide film was formed. Then, 2 mg of the surface-treating agent (i.e., containing 0.4 mg of the compound (B)) was deposited for each sheet of chemically strengthened glass (55 mm×100 mm). Subsequently, the chemically strengthened glass provided with the deposited film was heated in a temperature-constant chamber in the air at 140° C. for 30 minutes. Thereby, the deposited film was cured and a substrate (1) including a surface-treating layer was obtained.

Example 2

A substrate (2) was obtained in the same manner as in Example 1, except that the PFPE-containing compound (D) obtained in Synthesis Example 3 was used.

Example 3

A substrate (3) was obtained in the same manner as in Example 1, except that the PFPE-containing compound (J) obtained in Synthesis Example 4 was used.

Comparative Examples 1 to 4

Substrates (4) to (7) were obtained in the same manner as in Example 1, except that the PFPE-containing compound (B) was changed to the following control compounds (E), (F), (G), and (H).

Control Compound (E)

[Chem. 34]

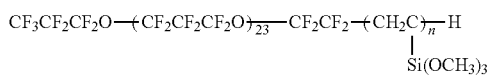

(n = 1~6)

Control Compound (F)

 [Chem. 35]

Control Compound (G)

[Chem. 36]

(m = 22, n = 19)

Control Compound (H)

[Chem. 37]

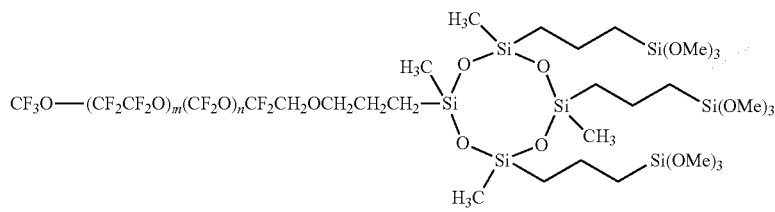

(m = 22, n = 19)

(Evaluation by Accelerated Weathering Test)

The substrates (1) to (7) obtained in Examples 1, 2, and 3 and Comparative Examples 1 to 4 were subjected to an accelerated weathering test. The accelerated weathering test is a test including UVB irradiation as follows. UVB irradiation was performed such that a UVB-313 lamp (Q-Lab Corp., irradiance at 310 nm: 0.63 W/m$^2$) was prepared; the surface-treating layer of the substrate was placed apart from the lamp by 5 cm; and the temperature of a plate carrying the substrate was 63° C. UVB irradiation was performed continuously. Upon measurement of the static contact angle with water, the substrate was briefly taken out, the surface-treating layer was wiped five reciprocations with Kimwipe (trade name, Jujo-Kimberly Co., Ltd.) sufficiently impregnated with pure water, then wiped five reciprocations with another Kimwipe sufficiently impregnated with ethanol, and subsequently dried. The static contact angle with water was measured immediately thereafter.

<Method of Measuring Static Contact Angle with Water>

The static contact angle with water was determined by the following method using a fully automatic contact angle meter DropMaster 700 (Kyowa Interface Science Co., Ltd.). To the substrate placed horizontally was dropped 2 μL of water from a micro syringe, and a still image was taken with a video microscope one second after the dropping. Then, the static contact angle with water was measured. The static contact angle with water was measured at five different points in the UVB-irradiated region of the surface-treating layer on the substrate, and the average value thereof was defined as the measured static contact angle with water.

The parameters in the examples were determined by the following methods.

For initial evaluation, the static contact angle with water of the substrate provided with the surface-treating layer was measured before UVB irradiation (UV irradiation time: 0 hours). Then, the surface-treating layer was irradiated with UVB for predetermined periods of time, and the static contact angle with water was measured after each period of time. The evaluation was performed at every 24 hours from the start of UVB irradiation until the static contact angle with water was below 80 degrees or the accumulated irradiation time reached 600 hours. The results are shown in Table 1.

TABLE 1

| Accumulated UVB Irradiation time (hr) | Static contact angle with water (degrees) | | | | | | |
|---|---|---|---|---|---|---|---|
| | Example 1 Substrate (1) | Example 2 Substrate (2) | Example 3 Substrate (3) | Comparative Example 1 Substrate (4) | Comparative Example 2 Substrate (5) | Comparative Example 3 Substrate (6) | Comparative Example 4 Substrate (7) |
| 0 | 116 | 115 | 115 | 115 | 115 | 115 | 115 |
| 24 | 115 | 114 | 115 | 115 | 114 | 113 | 114 |
| 48 | 115 | 114 | 116 | 112 | 105 | 102 | 111 |
| 72 | 114 | 113 | 114 | 108 | 99 | 94 | 105 |
| 96 | 114 | 113 | 114 | 62 | 61 | 60 | 99 |
| 120 | 114 | 112 | 113 | | | | 85 |
| 144 | 114 | 112 | 113 | | | | 70 |
| 168 | 114 | 111 | 112 | | | | |
| 192 | 113 | 111 | 112 | | | | |
| 216 | 113 | 110 | 111 | | | | |
| 240 | 113 | 110 | 111 | | | | |
| 264 | 113 | 110 | 111 | | | | |
| 288 | 113 | 109 | 110 | | | | |
| 312 | 113 | 108 | 109 | | | | |
| 336 | 112 | 107 | 109 | | | | |
| 360 | 112 | 106 | 108 | | | | |
| 384 | 111 | 104 | 107 | | | | |
| 408 | 111 | 102 | 107 | | | | |
| 432 | 111 | 100 | 106 | | | | |
| 456 | 110 | 97 | 106 | | | | |
| 480 | 109 | 93 | 105 | | | | |
| 504 | 107 | 88 | 103 | | | | |
| 528 | 106 | 83 | 101 | | | | |
| 552 | 105 | 79 | 97 | | | | |
| 576 | 102 | | 93 | | | | |
| 600 | 101 | | | | | | |

The results shown in Table 1 demonstrate that the substrates provided with the respective surface-treating layers formed from the PFPE-containing compounds of Examples 1, 2, and 3 significantly prevented a reduction in contact angle due to UV irradiation and maintained high water-repellency for a long period of time in comparison with the substrates provided with the respective surface-treating layers formed from the silane compounds of Comparative Examples 1 to 4. This is presumably because the surface-treating layers of the substrates formed in Examples 1, 2, and 3 were less likely to be decomposed by UV irradiation.

Examples 4, 5, and 6 and Comparative Examples 5, 6, 7, and 8

(Evaluation by Steel Wool Friction Durability)

For initial evaluation, the static contact angle with water of each of the substrates (1) to (7) provided with the respective surface-treating layers formed in Examples 1, 2, and 3 and Comparative Examples 1 to 4 was measured after the surface-treating layer was formed and no object was brought into contact with the surface thereof (number of frictional actions: zero). Then, the steel wool friction durability evaluation was performed. Specifically, the substrate provided with the surface-treating layer was placed horizontally and steel wool (grade: #0000, dimensions: 5 mm×10 mm×10 mm) was brought into contact with the surface-treating layer of the substrate. A load of 1000 gf was applied thereto and the steel wool was reciprocated at a rate of 140 mm/sec with the load. The static contact angle with water (degrees) was measured for every 2000 reciprocations, and the evaluation was finished after the measured contact angle was below 100 degrees. The results are shown in Table 2 as Examples 4, 5, and 6 and Comparative Examples 5, 6, 7, and 8 (in the table, the symbol "-" means "not measured").

TABLE 2

| | Static contact angle with water (degrees) | | | | | | |
| --- | --- | --- | --- | --- | --- | --- | --- |
| Number of reciprocations (times) | Example 4 Substrate (1) | Example 5 Substrate (2) | Example 6 Substrate (3) | Comparative Example 5 Substrate (4) | Comparative Example 6 Substrate (5) | Comparative Example 7 Substrate (6) | Comparative Example 8 Substrate (7) |
| 0 | 116 | 115 | 115 | 115 | 115 | 115 | 115 |
| 2000 | 112 | 113 | 113 | 110 | 101 | 108 | 107 |
| 4000 | 110 | 111 | 111 | 104 | 86 | 96 | 95 |
| 6000 | 108 | 110 | 110 | 92 | — | — | — |
| 8000 | 107 | 109 | 109 | — | | | |
| 10000 | 106 | 108 | 109 | | | | |
| 12000 | 104 | 106 | 108 | | | | |
| 14000 | 102 | 105 | 106 | | | | |
| 16000 | 100 | 103 | 104 | | | | |
| 18000 | 94 | 99 | 103 | | | | |
| 20000 | — | — | 102 | | | | |

The results shown in Table 2 demonstrate that the substrates provided with the respective surface-treating layers formed from the perfluoropolyether group-containing silane compounds of Examples 4, 5, and 6 exhibited improved friction durability.

INDUSTRIAL APPLICABILITY

The substrates of the invention each can suitably be used for windshields, side windows, rear windows, mirrors, applications relating to onboard devices such as sensor camera lenses, applications relating to information terminals such as displays, applications relating to building materials such as windowpanes, exterior security cameras, surveillance cameras, taps for waterworks, and showerheads. The substrates of the invention each exhibit high UV resistance, as well as water-repellency, oil-repellency, antifouling property, waterproof property, and high friction durability. Thus, they can suitably be used for exterior applications requiring weather resistance such as, but not limited to, antifouling coating substrates and waterproof coating substrates.

The substrates of the invention each can suitably be used for optical members, optical glass members for touchscreens, optical lens members such as onboard cameras and cameras for monitors, optical materials, optical members, medical equipment, and medical materials.

Preferred examples of the optical material include optical materials relating to displays to be mentioned below, as well as a wide variety of optical materials, such as displays, including cathode ray tubes (CRTs, e.g., TVs and monitors for personal computers), liquid crystal displays, plasma displays, organic EL displays, inorganic thin-film EL dot matrix displays, rear projection displays, vacuum fluorescent displays (VFDs), and field emission displays (FEDs); protective plates therefor, and those prepared by subjecting a surface thereof to an antireflection film treatment.

Examples of the optical member include: lenses of eyeglasses; front surface protective plates, antireflection plates, polarizing plates, and anti-glare plates for displays such as PDPs and LCDs; touchscreen sheets for devices such as mobile phones and personal digital assistants; disc surfaces of optical discs such as Blu-ray® discs, DVDs, CD-Rs, and MO discs; and optical fibers.

The substrates of the invention each can suitably be used for windowpanes for vehicles and windowpanes for buildings.

Examples of the windowpanes for vehicles include windshields, side windows, rear windows, quarter windows, side view mirrors, quarter windows, and side view mirrors of vehicles.

Examples of the windowpanes for buildings include interior or exterior windowpanes for buildings.

The substrates of the invention each can suitably be used for glasses and lenses of eyeglasses, watches, and swimming goggles, glass covers of devices and apparatuses, motorcycle helmets and windshields for helmets, glass lenses such as telescope lenses and camera lenses, glass safety screens, transparent separation equipment such as spray protective walls, glass doors or windows or plastic windows for devices or apparatuses such as chemical reaction hoods, biological or medical hoods, culture vessels, cabinets, microwave ovens, toaster ovens, and refrigerators, display windows, and security glasses.

The invention claimed is:

1. A substrate comprising a surface-treating layer, the surface-treating layer containing a compound represented by the following formula (1):

[Chem. 1]

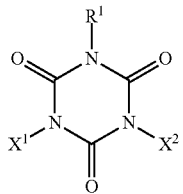

wherein
R$^1$ is a monovalent organic group other than those containing a urethane bond represented by R$^3$—(OR$^2$)$_a$-L-, wherein (OR$^2$)$_a$ is a polyether chain; R$^3$ is an alkyl group or a fluorinated alkyl group; and L is —C$_2$H$_4$—, —C$_3$H$_6$—, —CO—O—CH$_2$—CH(OH)—CH$_2$—, —(CF$_2$)$_n$—, wherein n is an integer of 0 to 4, —CH$_2$—, —C$_4$H$_8$—, or —(CF$_2$)$_n$—(CH$_2$)$_m$—, wherein n and m are each independently an integer of 0 to 4;
X$^1$ is a monovalent Si-containing group containing a hydrolyzable group; and
X$^2$ is a monovalent group,
the polyether chain being a chain represented by the following formula:

—(OC$_6$F$_{12}$)$_{m11}$—(OC$_5$F$_{10}$)$_{m12}$—(OC$_4$F$_8$)$_{m13}$—(OC$_3$X$^{10}$$_6$)$_{m14}$—(OC$_2$F$_4$)$_{m15}$—(OCF$_2$)$_{m16}$— wherein
m11, m12, m13, m14, m15, and m16 are each independently an integer of 0 or 1 or greater;
X$^{10}$s are each independently H, F, or Cl; and
the repeating units are present in any order.

2. The substrate according to claim 1, wherein the substrate is a glass substrate.

3. The substrate according to claim 2, wherein the glass substrate is a sapphire glass substrate, a soda-lime glass substrate, an alkali aluminum silicate glass substrate, a borosilicate glass substrate, an alkali-free glass substrate, a lead glass substrate, or a quartz glass substrate.

4. The substrate according to claim 1, wherein the substrate exhibits a static contact angle with water of 100 degrees or greater after a 400-hour accelerated weathering test performed under the following conditions:
<conditions of accelerated weathering test>
preparing a UVB-313 lamp exhibiting an irradiance of 0.63 W/m$^2$ at a wavelength of 310 nm; placing the surface-treating layer of the substrate apart from the lamp by 5 cm; and after every 24-hour irradiation, wiping the surface-treating layer with a cloth impregnated with water and with a cloth impregnated with ethanol, followed by drying.

5. The substrate according to claim 1, wherein the substrate exhibits a static contact angle with water of 110 degrees or greater after a 250-hour accelerated weathering test performed under the following conditions:
<conditions of accelerated weathering test>
preparing a UVB-313 lamp exhibiting an irradiance of 0.63 W/m$^2$ at a wavelength of 310 nm; placing the surface-treating layer of the substrate apart from the lamp by 5 cm; and after every 24-hour irradiation, wiping the surface-treating layer with a cloth impregnated with water and with a cloth impregnated with ethanol, followed by drying.

6. The substrate according to claim 1, wherein the substrate exhibits a static contact angle with water of 100 degrees or greater after 6000 processes of steel wool friction durability evaluation performed under the following conditions:
<conditions of steel wool friction durability evaluation>
bringing #0000-grade steel wool having dimensions of 5 mm×10 mm×10 mm into contact with the surface-treating layer of the substrate; applying a load of 1000 gf thereto; and reciprocating the steel wool at a rate of 140 mm/sec with the load, where one reciprocating motion is counted as one process.

* * * * *